United States Patent
Xu et al.

(10) Patent No.: US 12,305,213 B2
(45) Date of Patent: *May 20, 2025

(54) HIGH GRAVITY, FED-BATCH IONIC LIQUID BASED PROCESS FOR DECONSTRUCTING BIOMASS

(71) Applicant: NATIONAL TECHNOLOGY & ENGINEERING SOLUTIONS OF SANDIA, LLC, Albuquerque, NM (US)

(72) Inventors: Feng Xu, Albany, CA (US); Blake Simmons, San Francisco, CA (US); Seema Singh, Clarksburg, MD (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 764 days.

This patent is subject to a terminal disclaimer.

(21) Appl. No.: 17/473,906

(22) Filed: Sep. 13, 2021

(65) Prior Publication Data

US 2022/0170053 A1 Jun. 2, 2022

Related U.S. Application Data

(63) Continuation of application No. 15/777,649, filed as application No. PCT/US2016/063195 on Nov. 21, 2016, now Pat. No. 11,118,197.

(60) Provisional application No. 62/257,647, filed on Nov. 19, 2015.

(51) Int. Cl.
| | |
|---|---|
| *C12P 19/02* | (2006.01) |
| *C12P 7/10* | (2006.01) |
| *C12P 19/14* | (2006.01) |
| *C13K 1/02* | (2006.01) |
| *C13K 13/00* | (2006.01) |

(52) U.S. Cl.
CPC ............... *C12P 7/10* (2013.01); *C12P 19/02* (2013.01); *C12P 19/14* (2013.01); *C13K 1/02* (2013.01); *C13K 13/002* (2013.01); *C12P 2201/00* (2013.01); *C12P 2203/00* (2013.01); *Y02E 50/10* (2013.01)

(58) Field of Classification Search
CPC .. C12P 7/10; C12P 19/02; C12P 19/14; C12P 2203/00; C12P 2201/00; C13K 1/02; C13K 13/002; Y02E 50/10
See application file for complete search history.

(56) References Cited

U.S. PATENT DOCUMENTS

| | | | |
|---|---|---|---|
| 11,118,197 | B2 | 9/2021 | Xu et al. |
| 2008/0190013 | A1 | 8/2008 | Argyropoulos |
| 2011/0033906 | A1 | 2/2011 | Jo et al. |
| 2012/0111514 | A1 | 5/2012 | Dottori et al. |
| 2012/0301948 | A1 | 11/2012 | Brennan et al. |
| 2017/0247729 | A1 | 8/2017 | Liszka et al. |

FOREIGN PATENT DOCUMENTS

| | | |
|---|---|---|
| AU | 2008208870 B2 | 7/2008 |
| CN | 103849665 A | 6/2014 |

OTHER PUBLICATIONS

Hou, et al., "Evaluation of Toxicity and Biodegradability of Cholinium Amino Acids Ionic Liquids," PLoS ONE 2013, 8:3, pp. 1-7.
Xia, et al., "Aqueous Ionic Liquids and Deep Eutectic Solvents for Cellulosic Biomass Pretreatment and Saccharification," RSC Advances, Jan. 2014, 4:21, 10586-10596 (25 pages).

*Primary Examiner* — Louise W Humphrey
*Assistant Examiner* — Anjali Ajit Hirani
(74) *Attorney, Agent, or Firm* — Kilpatrick Townsend & Stockton LLP

(57) ABSTRACT

In one aspect, the present invention provides methods for preparing a fermentation product. The methods include pre-treating a mixture of biomass and ionic liquid, wherein the ionic liquid comprises a choline cation and the biomass comprises polysaccharide and lignin. The methods further include forming hydrolysates from the introduction of glycoside hydrolase to the pre-treated mixture at conditions sufficient to produce a sugar composition mixture for fermentation steps. The present invention provides methods for loading biomass mixtures in a batch-fed process, wherein the biomass slurries can be loaded into water or a concentrated sugar composition for hydrolysate production. The methods can be performed in a one-pot process, wherein the ionic liquids are present in the mixtures throughout each step. Aspects of the invention provide compositions of sugar composition mixtures and fermentation product mixtures.

7 Claims, 12 Drawing Sheets

HIGH GRAVITY, FED-BATCH IONIC LIQUID BASED PROCESS FOR DECONSTRUCTING BIOMASS

CROSS-REFERENCES TO RELATED APPLICATIONS

The present application is a continuation of U.S. patent application Ser. No. 15/777,649, filed May 18, 2018 and issued Sep. 14, 2021 as U.S. Pat. No. 11,118,197; which is a U.S. national stage entry of International Pat. Appl. No. PCT/US2016/063195, filed Nov. 2, 2016; which claims priority to U.S. Provisional Pat. Appl. No. 62/257,647, filed Nov. 19, 2015; which applications are incorporated herein by reference in their entirety.

STATEMENT AS TO RIGHTS TO INVENTIONS MADE UNDER FEDERALLY SPONSORED RESEARCH AND DEVELOPMENT

The invention was made with government support under Contract No. DE-AC02-05CH11231 awarded by the U.S. Department of Energy. The government has certain rights in the invention.

BACKGROUND OF THE INVENTION

Through the years, tremendous efforts have been made to develop biofuels from lignocellulosic biomass, which is derived from agricultural wastes, forest residues, and dedicated energy crops. However, one of the greatest limitations facing the economic viability of this technology is the recalcitrant nature of the lignocellulosic biomass to enzymatic hydrolysis into its component sugars. This resistance to breakdown necessitates the use of pre-treatment steps to enhance the accessibility to and hydrolysis of the carbohydrate components present in the lignocellulosic biomass. Pre-treatment processes involving ionic liquids (ILs) can require lower energy inputs and do not involve the use of specialized equipment.

Ionic liquids allow for the solubilization of crystalline cellulose and biomass under relatively mild conditions. However, ionic liquids are expensive and the pre-treatment process is both energy and time intensive. Furthermore, conventional ionic liquid pre-treatment processes involved in the production of concentrated sugars and fermentation products require a water-wash step, which can result in the loss of fermentable sugars and generate large volumes of waste water. As such, what is needed is a one-pot process for high gravity biomass processing that includes ionic liquids in the pre-treatment, saccharification, and yeast fermentation steps for the production of fermentable sugars and fermented products. The present invention addresses these and other needs.

BRIEF SUMMARY OF THE INVENTION

In one aspect, the present invention provides a method for producing a fermentation product from biomass, wherein the biomass comprises polysaccharide and lignin. In one aspect, the method comprises:
(i) providing a pre-treatment mixture comprising the biomass at a concentration of at least about 5% (w/w) and less than about 50%, an ionic liquid or mixture of ionic liquids at a concentration of between about 5% (w/w) and about 25% (w/w), and water, wherein the ionic liquid and biomass are present in the pre-treatment mixture at a mass ratio $R_{m/i}$ of from about 0.2 to about 5, and wherein the ionic liquid or mixture thereof comprises:
  a) a choline cation; and
  b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion;
(ii) maintaining the mixture under pre-treatment conditions sufficient to dissolve at least a portion of the polysaccharide present in the biomass, wherein the pre-treatment conditions comprise a temperature of at least about 100° C. and less than about 200° C. for a duration of at least about 0.5 h, thereby forming a mixture comprising pre-treated biomass and the ionic liquid or mixture of ionic liquids;
(iii) adding to the mixture comprising the pre-treated biomass and the ionic liquid or mixture of ionic liquids, a glycoside hydrolase and water under conditions sufficient to hydrolyze at least a portion of the polysaccharide present in the pre-treated biomass, thereby forming a mixture comprising a sugar composition and the ionic liquid or mixture of ionic liquids, wherein the sugar composition comprises at least one monosaccharide or oligosaccharide; and
(iv) fermenting the mixture comprising the sugar composition and the ionic liquid or mixture of ionic liquids with a fermentation microorganism under conditions suitable to produce the fermentation product,
wherein at least 70% of glucan and/or xylan present in the biomass is converted into the fermentation product In another aspect, the present invention provides a method of producing a polysaccharide hydrolysate from biomass, wherein the biomass comprises polysaccharide and lignin. In one aspect, the method comprises:
(i) providing a slurry comprising pre-treated biomass at a concentration of at least about 5% (w/w) and less than about 50% (w/w), an ionic liquid or mixture of ionic liquids at a concentration of between about 5% (w/w) and about 25% (w/w), and water, wherein the ionic liquid and biomass are present in the pre-treated slurry at a mass ratio $R_{m/i}$ of from about 0.2 to about 5, and wherein the ionic liquid or mixture thereof comprises:
  a) a choline cation; and
  b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion, wherein the mixture optionally comprises a glycoside hydrolase;
(ii) introducing a portion of the pre-treated biomass slurry to a mixture comprising water and optionally the glycoside hydrolase, thereby forming a mixture comprising a portion of the pre-treated biomass slurry, the glycoside hydrolase, and water;
(iii) maintaining the mixture comprising a portion of the pre-treated biomass slurry, the glycoside hydrolase, and water under conditions sufficient to hydrolyze the polysaccharide present in the portion of the pre-treated biomass, thereby forming a mixture comprising a hydrolyzed polysaccharide;
(iv) adding to the mixture comprising the hydrolyzed polysaccharide an additional portion of the pre-treated biomass slurry of step (i), and maintaining the mixture comprising the hydrolyzed polysaccharide under conditions sufficient to hydrolyze the polysaccharide present in the mixture; and
(v) optionally repeating the step of (iv) 1 to 100 times, wherein at least 70% of glucan and/or xylan present in the biomass is converted into a monosaccharide.

Another aspect of the present invention provides a method of producing a polysaccharide hydrolysate from biomass, wherein the biomass comprises polysaccharide and lignin. In one aspect, the method comprises:
(i) providing a slurry comprising pre-treated biomass at a concentration of at least about 5% (w/w) and less than about 50% (w/w), an ionic liquid or mixture of ionic liquids at a concentration of between about 5% (w/w) and about 25% (w/w), and water, wherein the ionic liquid and biomass are present in the pre-treated slurry at a mass ratio $R_{m/i}$, of from about 0.2 to about 5, and wherein the ionic liquid or mixture thereof comprises:
  a) a choline cation; and
  b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion, wherein the mixture optionally comprises a glycoside hydrolase;
(ii) introducing a portion of the pre-treated biomass slurry to a mixture comprising a sugar composition and optionally the glycoside hydrolase, wherein the sugar composition is at a concentration of at least 70% (w/w), thereby forming a mixture comprising a portion of the pre-treated biomass slurry, the glycoside hydrolase, and the sugar composition;
(iii) maintaining the mixture comprising the portion of the pre-treated biomass slurry, the glycoside hydrolase, and the sugar composition under conditions sufficient to hydrolyze polysaccharide present in the portion of the pre-treated biomass, thereby forming a further mixture comprising hydrolyzed polysaccharide;
(iv) adding to the further mixture comprising the hydrolyzed polysaccharide an additional portion of the pre-treated biomass slurry of step (i), and maintaining the further mixture comprising the hydrolyzed polysaccharide under conditions sufficient to hydrolyze the polysaccharide present in the mixture; and
(v) optionally repeating the step of (iv) 1 to 100 times, wherein at least 70% of glucan and/or xylan present in the biomass is converted into a monosaccharide.

In one aspect, the present invention provides a sugar composition mixture. In one aspect, the mixture is comprised of at least one monosaccharide or oligosaccharide, a pre-treated biomass, an ionic liquid or mixture of ionic liquids at a concentration of between about 5% (w/w) and about 25% (w/w), and water, wherein the ionic liquid or mixture thereof comprises:
  a) a choline cation; and
  b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion.

In another aspect, the present invention provides a fermentation product mixture. In one aspect, the mixture is comprised of at least a fermentation organism, a fermentation product, an ionic liquid or mixture of ionic liquids at a concentration of between about 5% (w/w) and about 25% (w/w), and water, wherein the ionic liquid or mixture thereof comprises:
  a) a choline cation; and
  b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion.

Further aspects and embodiments of the invention are described in detail below.

DETAILED DESCRIPTION OF THE INVENTION

I. Introduction

Figure 1:
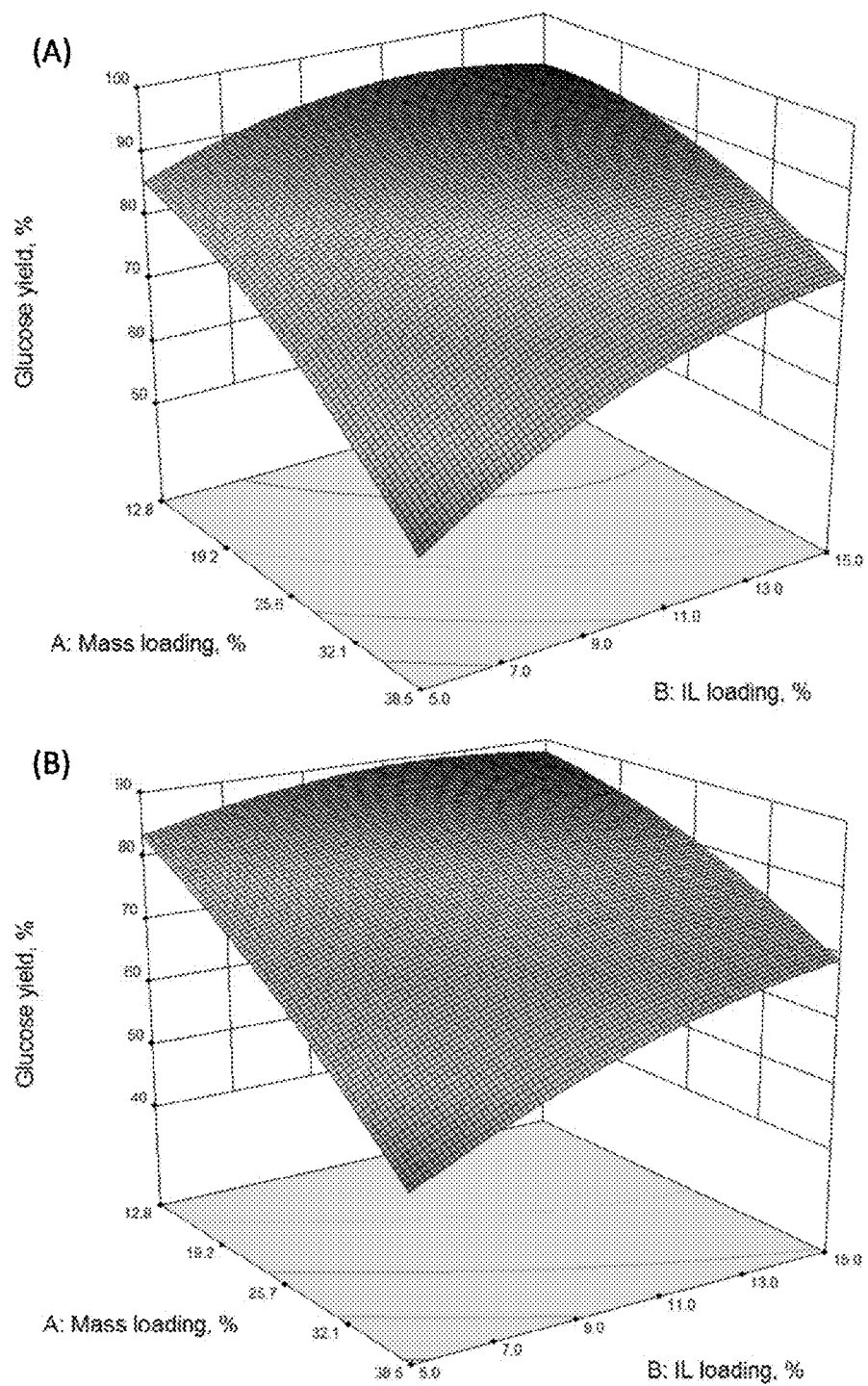
FIG. 1. 3-D plots of glucose yields after one-pot pre-treatment and saccharification. (A) Yields with [Ch][Lys] pre-treatment; (B) Yields with [Ch]$_2$[Asp] pre-treatment.

Second-generation biofuel production from lignocellulosic biomass is currently challenging as most of the processes in use are constrained by factors such as low titer and high water usage. Industrial ethanol production requires an ethanol titer of more than 40 g $L^{-1}$ for efficient distillation.[1,2] It is therefore necessary to use a high glucan loading (e.g., over 8 wt %) or use an engineered microbe that is able to efficiently convert both pentose and hexose[3]. High-gravity (HG) biomass processing has been frequently reported to reach this titer. For instance, with acid pre-treatment followed by a water-washing step, an ethanol titer of 57 g $L^{-1}$ was obtained with simultaneous saccharification and fermentation (SSF).[4] However, that process required a large quantity of water for the removal of toxic chemicals from the pre-treated biomass before saccharification.

A one-pot process has been employed in many biochemical processes because of its relative simplicity, resulting in lower operating and capital costs.[5] In terms of one-pot biofuel production from lignocellulosic biomass, progress has so far been limited to the conversion of cellulose substrates, not lignocellulosic biomass. Cellulase-displaying yeast has been employed to directly ferment ethanol from cellulose.[6] It was also reported that ethanol could be fermented from Solka-Floc (powdered cellulose) by using a co-culture in a one-pot process scheme.[7]

Until now, the production of biofuels from lignocellulose using a one-pot conversion technology that includes pre-treatment, saccharification, and fermentation has not been reported because of the significant technical challenges present. For example, the degradation products generated during dilute acid pre-treatment (e.g., Hydroxymethylfurfural (HMF) and furfural) must be removed before enzymatic hydrolysis of pre-treated biomass as HMF inhibits the enzymes used.[8] In addition, the solvents or chemicals used for pre-treatment are usually toxic to the microbes and enzymes used downstream to complete the biomass conversion process, and the removal/recycle of these reaction agents can be costly.[9] Because sulfuric acid used in acid pre-treatment is not economical to recycle, it must be removed and disposed of using strategies that generate large quantities of solid waste or wastewater and, in some cases, result in unacceptable sugar losses or require energy- and greenhouse gas (GHG)-intensive inputs such as ammonia.[10]

The development of robust one-pot biomass conversion technologies operating at high solids loading can reduce biorefinery capital costs, operating costs, waste generation, and impacts on the climate and local natural resources. However, there remain engineering challenges that must be addressed before HG biomass processing could be applied using the one-pot process approach. These challenges include: 1) The mass transfer limitation that exists throughout pre-treatment, saccharification, and fermentation unit operations due to the water constraint; 2) The generation of inhibitory products at high solid loading could pose problems for downstream processing,[11] and concentrated end-products (e.g., glucose, cellobiose) may decrease overall enzyme activity;[12] 3) Decreased viability of microorganisms due to the increased osmolarity as a result of high concentration of carbon substrates (e.g., glucose and xylose) and related end products.[2]

Recently, significant progress has been made with ionic liquid (IL) pre-treatment, and a one-pot process has been successfully demonstrated for biomass-sugar production that combines pre-treatment and saccharification.[13] Here we report methods and compositions that use biocompatible and bio-derived ILs (e.g., choline-based ILs) for one-pot processing that can combine pre-treatment, saccharification, and fermentation of biomass into desired end products, such as biofuels.[14,15]

II. Definitions

As used herein, the terms "fermenting," "fermentation," and "fermentation product" refer to a metabolic process performed by an organism or microorganism that converts one substrate to another, such as when an organism or microorganism utilizes glucose and converts it to a fermentation product (e.g., ethanol or propionic acid). In the present invention "fermentation" is typically used broadly to refer to the conversion of simple sugars to a desired product.

As used herein, the term "biomass" and "polysaccharide biomass" are used interchangeably to refer to plant-based material that includes a plurality of components such as lignin, cellulose, and hemicellulose. Sources of biomass includes trees, shrubs, grasses, wheat, wheat straw, sugar cane bagasse, corn, corn husks, corn kernel including fiber from kernels, products and by-products from milling of grains such as corn, rice, wheat, and barley, as well as municipal solid waste, waste paper, and yard waste. Biomass sources can also include herbaceous material, agricultural residues, forestry residues, and paper mill residues. Additional examples include branches, bushes, canes, corn and corn husks, energy crops, forests, fruits, flowers, grains, grasses, herbaceous crops, leaves, bark, needles, logs, roots, saplings, short rotation woody crops, shrubs, switchgrasses, trees, vegetables, fruit peels, vines, sugar beet pulp, wheat midlings, oat hulls, hard and soft woods, organic waste materials generated from agricultural processes including farming and forestry activities, or mixtures thereof.

As use herein, the term "lignin" refers to a phenylpropane polymer of monolignol monomers (p-coumaryl alcohol, coniferyl alcohol, and sinapyl alcohol) found as an integral part of the secondary cell walls of plants and certain types of algae.

As used herein, the term "lignocellulosic biomass" refers to natural and/or synthetic materials containing lignin and cellulose. Lignocellulosic biomass can also contain hemicellulose. Generally, these materials also contain (but need not contain) xylan, protein, and/or other carbohydrates, such as starch.

As used herein, the term "cellulose" refers to a homopolymer of β(1→4) linked D-glucose units that form a linear chain. Cellulose can contain several hundred to several thousand or more glucose units, making cellulose a polysaccharide.

As used herein, the term "hemicellulose" refers to a heteropolymer containing different saccharide units, including but not limited to, xylose, mannose, galactose, rhamnose and arabinose. Hemicellulose forms a branched polymer with several hundred to several thousand sugar units. Hemicellulose can include both pentose and hexose sugars.

As used herein, the term "polysaccharide" generally refers to a compound containing 10 or more sugars linked together as described for oligosaccharides.

As used herein, the term "oligosaccharide" refers to a compound containing at least two sugars covalently linked together. Oligosaccharides include disaccharides, trisaccharides, tetrasaccharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon (the anomeric carbon) and the 3-carbon of adjacent sugars (i.e., a 1-3 linkage), the 1-carbon (the anomeric carbon) and the 6-carbon of adjacent sugars (i.e., a 1-6 linkage), or the 1-carbon (the anomeric carbon) and the 2-carbon of adjacent sugars (i.e., a 1-2 linkage). Other linkages can be present in the oligosaccharide, depending on the particular sugar subunits present. Those of skill in the art will appreciate that a sugar can be linked within an oligosaccharide such that the glycosidic bond at the anomeric carbon is in the α- or β-configuration.

As used herein, the term "ionic liquid" refers to an organic salt that is a liquid at room temperature rather than a solid or crystalline substance. Ionic liquids typically exhibit a number of advantageous properties, including low volatility, thermal stability, and the ability to dissolve a wide range of solutes under mild conditions.

As used herein, the terms "choline" and "cholinium" refer to the 2-hydroxy-N,N,N-trimethylethan-amonium cation and salts thereof (e.g., 2-hydroxy-N,N,N-trimethylethanamonium hydroxide). The term "cholinium acetate," also referred to as [Ch][OAc], refers to an ionic liquid having acetic acid anions and one choline cation for each one of the acetic acid anions. As used herein, the term "cholinium lysinate," also referred to as [Ch][Lys], refers to an ionic liquid having lysine anions and one choline cation for each one of the lysine anions. As used herein, the term "choline aspartate," also referred to as $[Ch]_2[Asp]$, refers to an ionic liquid having aspartic acid dianions and two choline cations for each one of the aspartic acid dianions.

As used herein, the term "carboxylic acid" refers to an alkane or alkene having one carboxy moiety (i.e., —COOH groups). As used herein, the term "carboxylic acid anion" refers to a carboxylic acid wherein the carboxy moiety is deprotonated (i.e., present as a —COO⁻ anion). Carboxylic acid anions are generally bound to cations in an ionic liquid via electrostatic interaction.

As used herein, the term "dicarboxylic acid" refers to and alkane or alkene having two carboxy moieties (i.e., —COOH groups). As used herein, the term "dicarboxylic acid anion" refers to a dicarboxylic acid wherein one or two of the carboxy moieties is deprotonated (i.e., present as a —COO⁻ anion). Dicarboxylic acid anions are generally bound to cations in an ionic liquid via electrostatic interaction.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. An "alkane" refers to the parent compound of the alkyl radicals described herein.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. An "alkene" refers to the parent compound of the alkenyl radicals described herein.

As used herein, the term "cation" refers to a positively charged molecule that pairs with an anion in an ionic liquid via electrostatic interaction. Examples of cations suitable for inclusion in ionic liquids include, but are not limited to, cholinium, ammonium, imidazolium, pyridinium, sulfonium, and phosphonium cations.

As used herein, the term "anion" refers to a negatively charged molecule that pairs with a cation in an ionic liquid via electrostatic interaction. Examples of anions suitable for inclusion in ionic liquids include, but are not limited to, carboxylic acid anion, dicarboxylic acid anion, lysinate, hydroxide, bisulfate, sulfate, hydrogen phosphate, dihydrogen phosphate, bicarbonate, and chloride anions.

As used herein, the terms "dissolve" and "dissolution" refer to the solvation of a solute with a solvent to form a solution. More particularly, dissolution refers to the partial or complete solubilization of biomass in an ionic liquid or an ionic liquid solution. In the methods of the invention, dissolution of lignocellulosic biomass can include partial or complete disruption of intra- and intermolecular hydrogen bonds present in cellulose polymer chains, partial or complete disruption of interactions between cellulose and hemicellulose, and partial or complete solubilization of lignin.

The terms "about" and "around," as used herein to modify a numerical value, indicate a close range surrounding that explicit value. If "X" were the value, "about X" or "around X" would indicate a value from 0.9X to 1.1X. "About X" thus includes, for example, a value from 0.95X to 1.05X. Any reference to "about X" or "around X" specifically indicates at least the values X 0.90X, 0.91X, 0.92X 0.93X, 0.94X, 0.95X, 0.96X, 0.97X 0.98X, 0.99X, 1.01X 1.02X, 1.03X, 1.04X 1.05X, 1.07X, 1.08X, 1.09X and 1.10X. Accordingly, "about X" and "around X" are intended to teach and provide written description support for a claim limitation of, e.g., "0.98X."

The terms "hydrolyze," "hydrolysis," and "saccharification," when used herein with respect to polysaccharide chemistry, refer to the cleavage of one or more glycosidic bonds in an oligosaccharide or a polysaccharide by water. The hydrolysis is typically catalyzed by an enzyme such as a glycoside hydrolase. Hydrolysis can also be promoted by addition of a catalyst such as a metal ion, and acid, a base, or a combination thereof.

As used herein, the term "glycoside hydrolase" refers to an enzyme that catalyzes the cleavage of the glycosidic linkage in oligosaccharides or polysaccharides by water to release smaller sugars.

As used herein, the term "sugar composition" refers to a mixture containing one or more monosaccharides, oligosaccharides, or combinations thereof. Sugar compositions prepared according to the methods of the invention are also referred to as "hydrolysates" in the present application.

As used herein, the term "monosaccharide" refers to a sugar having a five-membered carbon backbone (i.e., a pentose) or a six-membered carbon backbone (i.e., a hexose). Examples of monosaccharides include, but are not limited to, glucose, ribose, fucose, xylose, arabinose, galactose, mannose, glucuronic acid, and iduronic acid. Monosaccharides also include pentoses and hexoses substituted with hydroxy groups, oxo groups, amino groups, acetylamino groups, and other functional groups.

As used herein, the terms "percentage solution" and "% w/w" in the context of biomass loading of a solution and/or mixture described herein refers to the weight of biomass divided by the weight of the ionic liquid and water in the mixture, multiplied by 100. As an example, a mixture having a weight percent of 30% w/w biomass solids has 3 grams of biomass in 10 grams of a mixture of ionic liquid and water. As another example, adding 3 grams of a biomass solid to a 10% w/w ionic liquid water solution provides a mixture having 30% w/w biomass solids in a 3:1:9 ratio of biomass solids:ionic liquid:water.

As used herein, the terms "mass ratio" and "$R_{m/i}$" refers to the mass of the biomass in a mixture relative to the mass of ionic liquid solution in the mixture. As a non-limiting example, a mixture having an $R_{m/i}$ of 0.5 has a (biomass weight):(ionic liquid weight) ratio of 1:2, wherein the weight of the ionic liquid solution in the mixture is twice as much as the weight of the biomass in the mixture.

As used herein, the term "pH" refers to refers to a measurement of the concentration of hydrogen ions in a mixture such as an aqueous solution. pH is expressed as the decimal logarithm (i.e., $\log_{10}$) of the reciprocal of the hydrogen ion concentration in the mixture. The pH of a mixture can be determined using a number of known techniques. One of skill in the art will know how to adjust the pH of a mixture by adding acids and/or bases to the mixture.

As used herein, the term "acid" refers to a substance that is capable of donating a proton (i.e., a hydrogen cation) to form a conjugate base of the acid. Examples of acids include, but are not limited to, hydrochloric acid, sulfuric acid, acetic acid, and formic acid.

As used herein, the term "base" refers to a substance that is capable of accepting a proton (i.e., a hydrogen cation) to form a conjugate acid of the base. Examples of bases include, but are not limited to, sodium hydroxide, potassium hydroxide, sodium bicarbonate, and potassium carbonate.

III. Compositions

In one aspect, the present invention provides a fermentation product mixture. In typical embodiments, the fermentation product mixture is comprised of at least a fermentation organism, a fermentation product, an ionic liquid or mixture of ionic liquids at a concentration of between about 5% (w/w) and about 25% (w/w), and water, wherein the ionic liquid or mixture thereof comprises:
  a) a choline cation; and
  b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion.

Fermentation Product Mixture

Generally, the fermentation products of the fermentation product mixture are useful organic compounds such as biofuels, fine chemicals, food additives, pharmaceuticals, pharmaceutical intermediates, and the like. Examples of such products include, but are not limited to, alcohols (e.g., ethanol, methanol, butanol); organic acids (e.g., propionic acid, citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, β-carotene); fatty acids and fatty acid derivatives (as described, e.g., in PCT/US2008/068833); isoprenyl alkanoates (as described, e.g., PCT/US2008/068756, methyl butenol (as described, e.g., PCT/US2008/068831; fatty acid esters (as described, e.g., in PCT/US2010/033299), isoprenoid-based alternative diesel fuel (as described, e.g., in PCT/US2011/059784; a polyketide synthesized by a polyketide synthase, such as a diacid (see, e.g., PCT/US2011/061900), biofuels (see, e.g., PCT/US2009/042132), or alpha-olefins (see, e.g., PCT/US2011/053787), or combinations thereof.

In some embodiments, the fermentation organisms are employed for fermentation in the fermentation product mixture to produce a fermentation product. Organisms employed for fermentation may be wild-type organisms or may be genetically modified. Such organisms are well known and include bacteria, yeast, microalgae, and filamentous fungi. In some embodiments, the yeast is a *Saccharomyces* sp. e.g., *Saccharomyces cerevisiae* or *Saccharomyces uvarum*. Other yeasts may also be employed, e.g., *Kluyveromyces*, such as *Kluyveromyces marxianus*, *Kluyveromyces lactis* or *Kluyveromyces fragilis*; *Candida*, such as *Candida pseudotropicalis* or *Candida brassicae*; a *Hansenula*, *Pichia*, such as *Pichia pastoris*, *Saccharomyces*, *Schizosaccharomyces*, such as *Schizosaccharomyces pombe*, or *Yarrowia* sp. Examples of fermenting bacteria that may be used include *E. coli*, *Klebsiellan* sp., *Bacillus* sp., *Clostridium* sp., *Zymomonas* sp. and others (for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis*). Examples of filamentus fungi include *Aspergillus* sp., *Trichoderma* sp., Myceliopthera sp., and *Neurospora* sp.

In one aspect, the methods and compositions provided herein are surprisingly non-toxic to one or more fermentation organisms. Thus, for example, in certain embodiments, the fermentation organism of a fermentation product mixture is a viable fermentation microorganism. In some embodiments, the fermentation product mixture contains both viable and unviable fermentation microorganisms. The fermentation product mixture can contain, for example, from about 50% to about 99.9% or more viable microorganisms, or from about 50% to about 90% viable microorganisms, or from about 50% to about 80% viable microorganisms, or from about 50% to about 75% viable microorganisms, or from about 50% to about 70% viable microorganisms, or from about 50% to about 65% viable microorganisms, or from about 50% to about 60% viable microorganisms, or from about 50% to about 55% viable microorganisms, or from about 55% to about 95% viable microorganisms, or from about 60% to about 85% viable microorganisms, or from about 65% to about 80% viable microorganisms, or from about 70% to about 75% viable microorganisms. In some cases, at least about 50%, 75%, or 90% of the fermentation microorganisms of the fermentation product mixture are viable. In some cases, fermentation organism viability in a fermentation product mixture can be measured during a linear or exponential growth phase of the organism in a fermentation product mixture containing ionic liquids as described herein. In some cases, fermentation organism viability can be measured in a fermentation product mixture that contains a concentration or concentration range of fermentation product described herein.

Examples of fermentation products that can be obtained from the fermentation microorganisms in the fermentation product mixture include, but are not limited to: ethanol obtained from *Saccharomyces, Schizosaccharomyces, Saccharomycodes, Torulopsis, Kluyveromyces, Zymomonas mobilis*, or *E. coli*; tartaric acid obtained from Lactobacilli; itaconic acid obtained from *Aspergillus terreus* or *Aspergillus itaconicus*; succinic acid obtained from *Actinobacillus* sp. 130Z, *Anaerobiospirillum succiniproducens, Actinobacillus succinogenes*, or *E. coli*; hydroxypropionic acid obtained from *Lactobacillus delbrückii, L. leichmannii*, or *Sporolactobacillus inulinus*; propionic acid obtained from *Propionibacterium* or *Clostridium propionicum*; citric acid obtained from an *Aspergillus* sp., such as *Aspergillus niger* or *Aspergillus wentii*; aconitic acid obtained from *Aspergillus niger* or *Aspergillus wentii*; malic acid obtained from Aspergilli, *A. niger, A. oryzae*, or *Corynebacterium*; gluconic acid obtained from Aspergilli; butyric acid obtained from *Clostridium*; lactic acid obtained from *Lactobacillus*; eicosapentaenic acid obtained from *Mortiella, Phytium, Rhodopseudomonas*, or *Shewanella* spp.; propanediol obtained from *E. coli*; butanediol obtained from *Enterobacter aerogenes, Bacillus subtilis*, or *Klebsiella oxytoca*; butanol obtained from *Clostridium* spp.; glycerol obtained from *Saccharomyces rouxii*; mannitol obtained from *Aspergillus candida* or *Torulopsis mannitofaciens*; acetone obtained from *Clostridium*; and gibberellic acid obtained from *Gibberella fujikuroi*.

In some embodiments, the fermentation product in the fermentation product mixture is at a concentration of about 30 grams per liter to less than 1000 grams per liter, or at least 20 grams per liter. The fermentation product can be in the fermentation product mixture at concentrations of about 35 grams per liter to about 70 grams per liter, or about 40 grams per liter to about 70 grams per liter, or about 45 grams per liter to about 80 grams per liter, or about 50 grams per liter to about 85 grams per liter. In some embodiments, the fermentation product mixture comprises from about 0.5% to about 30% of the fermentation product, or from about 1% to about 25% of the fermentation product, or from about 2% to about 20% of the fermentation product, or from about 5% to about 30%, or from about 5% to about 20%, or from about 5% to about 15% of the fermentation product, or from about 5% to about 12% of the fermentation product, or from about 6% to about 15%, or from about 6% to about 10% of the fermentation product, or from about 10% to about 30% of the fermentation product, or from about 10% to about 20% of the fermentation product, or from about 6% to about 20% of the fermentation product.

Sugar Composition Mixture

In another aspect of the invention, a sugar composition mixture is provided. In some embodiments, the sugar composition mixture is comprised of at least one monosaccharide or oligosaccharide, a pre-treated biomass, an ionic liquid or mixture of ionic liquids at a concentration of between about 5% (w/w) and about 25% (w/w), and water, wherein the ionic liquid or mixture thereof comprises:

a) a choline cation; and b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion.

Sugar compositions, or hydrolysates, of the sugar composition mixture contain one or more monosaccharides and/or oligosaccharides. Monosaccharides present in the sugar compositions can include, but are not limited to, fucose, arabinose, rhamnose, galactose, mannose, xylose, glucose, glucuronic acid, and galacturonic acid. The oligosaccharides in the sugar compositions contain monosaccharide subunits (e.g., fucose, arabinose, rhamnose, galactose, mannose, xylose, glucose, glucuronic acid, and galacturonic acid) linked together via glycosidic bonds.

The pre-treated biomass of the sugar composition mixture is comprised biomass materials which have been maintained at conditions suitable to enhance the accessibility to and hydrolysis of the carbohydrate components present in the biomass. Biomass can include, but is not limited to, wood resources, municipal solid waste, wastepaper, and crop residues (see, for example, Wiselogel et al., 1995, in Handbook on Bioethanol (Charles E. Wyman, editor), pp. 105-118, Taylor & Francis, Washington D.C.; Wyman, 1994, Bioresource Technology 50: 3-16; Lynd, 1990, Applied Biochemistry and Biotechnology 24/25: 695-719; Mosier et al., 1999, Recent Progress in Bioconversion of Lignocellulosics, in Advances in Biochemical Engineering/Biotechnology, T. Scheper, managing editor, Volume 65, pp. 23-40, Springer-Verlag, New York). Other examples of biomass include, without limitation, crops such as starch crops (e.g., corn, wheat, or barley), sugar crops (e.g., sugarcane, energy cane or sugar beet), forage crops (e.g., grasses, alfalfa, or clover), and oilseed crops (e.g., soybean, sunflower, or safflower); wood products such as trees, shrubs, and wood residues (e.g., sawdust, bark or the like from forest clearings and mills); waste products such as municipal solid waste (MSW; e.g., paper, food and yard wastes, or wood), process waste, and paper sludge; and aquatic plants such as algae, water weeds, water hyacinths, or reeds and rushes. Other examples of biomass include sorghum, rice hulls, rice straw, wheat straw, and other straws.

In certain embodiments, the polysaccharide biomass comprises cellulose, hemicellulose, lignocellulose, or mixtures thereof. In some embodiments, the polysaccharide biomass comprises lignocellulose. Biomass materials typically contain a mixture of polysaccharide species. In many instances, the predominant polysaccharide in the primary cell wall of biomass is cellulose, the second most abundant is hemicellulose, and the third is pectin. The secondary plant cell wall, produced after the cell has stopped growing, can also contain other polysaccharides and is strengthened through polymeric lignin covalently cross-linked to hemicellulose.

Cellulose is a homopolymer of anhydrocellobiose and thus a linear β-(1-4)-D-glucan, while hemicelluloses include a variety of sugar subunits, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

In addition to the polysaccharides described above, polysaccharide biomass typically contains lignin. Lignin is a phenylpropane polymer of monolignol monomers. It is generally found as an integral part of the secondary cell walls of plants and certain types of algae. There are three monolignol monomers, methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Gymnosperms have a lignin that consists almost entirely of G with small quantities of H. That of dicotyledonous angiosperms is more often than not a mixture of G and S (with very little H), and monocotyledonous lignin is a mixture of all three. Many grasses have mostly G, while some palms have mainly S. All lignins contain small amounts of incomplete or modified monolignols, and other monomers are prominent in non-woody plants. Unlike cellulose and hemicellulose, lignin cannot be depolymerized by hydrolysis. Cleavage of the principal bonds in the lignin polymer generally proceeds through oxidation.

In some embodiments, the polysaccharide biomass is derived from corn stover, corn fiber, hard wood, softwood, cereal straw, switchgrass, *Miscanthus*, rice hulls, municipal solid waste (MSW), industrial organic waste, office paper, or mixtures thereof.

Sugar composition mixtures and/or hydrolysis mixtures described herein can contain one or more glycoside hydrolases. For example, the sugar composition mixtures and/or hydrolysis mixtures can contain a glycoside hydrolase (or a mixture of glycoside hydrolases) in an amount ranging from about 0.01 to about 10% (w/w), with respect to the amount of biomass used in the pre-treatment step. Thus, for example, when the method is conducted using 1 kg of biomass, for example, the hydrolysis step can be conducted with a glycoside hydrolase or a mixture of glycoside hydrolases in an amount ranging from about 100 mg to about 100 g. Those of skill in the art will appreciate that the amount of glycoside hydrolase or mixture of enzymes used in the methods of the invention will depend in part on factors including, but not limited to, the particular enzyme used, the nature of the biomass source, and the extent of the pre-treatment of the biomass solids used in the hydrolysis.

In certain embodiments, the sugar composition has a sugar titer (e.g., upon completion of a saccharification reaction) of from about 25 g/L to about 150 g/L, from about 30 g/L to about 100 g/L, from about 30 g/L to about 90 g/L, from about 40 g/L to about 85 g/L, or about 60, 70, or 80 g/L. In certain embodiments, the sugar composition has a sugar titer (e.g., upon completion of a saccharification reaction) of from about 30 g/L to about 100 g/L, from about 40 g/L to about 95 g/L, from about 45 g/L to about 90 g/L, or from about 50 g/L to about 85 g/L.

Ionic Liquids and Mixtures Thereof

A number of ionic liquids can be used in the invention. In general, the ionic liquid is suitable for pre-treatment of the biomass and compatible with glycoside hydrolases used for saccharification of cellulose, lignin, and other polysaccharides. The ionic liquids contain anions paired with cations via electrostatic interactions. In certain embodiments of the invention, the ionic liquid contains one mono-anion paired with one cation. In other embodiments, the ionic liquid contains one di-anion paired with two cations. In certain other embodiments of the invention, the ionic liquid contains one tri-anion paired with three cations.

In some embodiments, the anion is a carboxylic acid anion, dicarboxylic acid anion, lysinate, hydroxide anion, sulfate anion, bisulfate anion, dihydrogen phosphate anion, phosphate anion, bicarbonate anion, chloride anion, bromide anion, iodide anion, nitrate anion, trifluoromethanesulfonate anion, tetrafluoroborate anion, hexafluorophosphate anion, tetrachloroaluminate anion, dimethyl sulfate anion, dimethyl phosphate anion, a diethyl phosphate anion, or a mixture thereof. The carboxylic acid anion and the dicarboxylic acid anion can be substituted with from one to three substituents selected from amino, hydroxy, halo, and oxo. The hydroxyl, halo, amino, and oxy substituents can be on the same carbon atom or on different carbon atoms in the carboxylic acid anion and the dicarboxylic acid anion.

In some embodiments, the anion is a carboxylic acid anion, dicarboxylic acid anion, lysinate, hydroxide anion, bisulfate anion, dihydrogen phosphate anion, phosphate anion, bicarbonate anion, or a chloride anion. In some embodiments, the anion is selected from acetate, lysinate, or aspartate.

The ionic liquids of the invention can contain any suitable cation. Suitable cations include, but are not limited to, ammonium cations and imidazolium cations. Examples of ammonium cations include, but are not limited to, 2-hydroxyethyl-trimethylammonium, benzyldimethyltetradecylammonium, benzyltrimethylammonium, butyltrimethylammonium, choline, diethylmethyl(2-methoxyethyl) ammonium, ethyldimethylpropylammonium, methyltrioctadecylammonium, methyltrioctylammonium, tetrabutylammonium, tetradodecylammonium, tetraethylammonium, tetraheptylammonium, tetrahexadecylammonium, tetrahexylammonium, tetrakis(decyl)ammonium, tetramethylammonium, tetraoctylammonium, tributylmethylammonium, triethylmethylammonium, and tris(2-hydroxyethyl)methylammonium.

The imidazolium cations can be, but are not limited to, 1-alkyl-3-alkylimidazolium cations, wherein an "alkyl" is an alkyl group comprising from 1 to 10 carbon atoms. In some embodiments, the "alkyl" is a methyl group, ethyl group or butyl group. Examples of imidazolium cations include: 1-(2-hydroxyethyl)-3-methylimidazolium; 1-(3-cyanopropyl)-3-methylimidazolium; 1,2,3-trimethylimidazolium; 1,2-dimethyl-3-propylimidazolium; 1,3-bis(cyanomethyl) imidazolium; 1,3-diethoxyimidazolium; 1,3-dihydroxy-2-methylimidazolium; 1,3-dihydroxyimidazolium; 1,3-dimethoxy-2-methylimidazolium; 1,3-dimethoxyimidazolium; 1,3-dimethylimidazolium; 1-allyl-3-methylimidazolium; 1-benzyl-3-methylimidazolium; 1-butyl-2,3-dimethymidazolium; 1-butyl-3-methylimidazolium (BMIM); 1-decyl-3-methylimidazolium; 1-dodecyl-3-methylimidazolium; 1-ethyl-2,3-dimethylimidazolium (EDIM); 1-ethyl-3-methylimidazolium (EMIM); 1-hexyl-3-methylimidazolium; 1-methyl-3-octylimidazolium; 1-methyl-3-propylimidazolium; 1-methylimidazolium (MIM); and 4-(3-butyl-1-imidazolio)-1-butanesulfonate.

Other cations can be used in the ionic liquids of the present invention, including, but not limited to: pyridinium cations (e.g., N-ethylpyridinium, N-butylpyridinium, and the like); sulfonium cations (e.g., trimethylsulfonium, triethylsulfonium, tributylsulfonium, diethylmethylsulfonium, dimethylpropylsulfonium, dimethylhexylsulfonium, and the like); and phosphonium cations (e.g., tetramethylphosphonium, tetraethylphosphonium, tetrapropylphosphonium, tetrabutylphosphonium, tetraoctylphosphonium, tetraphenylphosphonium, trimethylethylphosphonium, triethylmethylphosphonium, hexyltrimethylphosphonium, trimethyloctylphosphonium, and the like).

In some embodiments, the cation is selected from choline, $(C_{1-18}\ \text{alkyl})_3NW$, $(C_{1-6}\ \text{alkyl})_x(C_{6-18}\ \text{alkyl})_yN^+$, $(C_{1-10}\ \text{alkyl})_z\text{imidazolium}$, $(C_{1-10}\ \text{alkyl})_z\text{pyrazolium}$, and mixtures thereof; wherein subscript x and subscript y are each 0, 1, 2, 3, or 4, and the sum of x and y is 4; and wherein each subscript z is 1, 2, or 3.

The cation can be, for example, $(C_{1-16}\ \text{alkyl})_3NH^+$, $(C_{1-12}\ \text{alkyl})_3NH^+$, $(C_{1-10}\ \text{alkyl})_3NH^+$, $(C_{1-8}\ \text{alkyl})_3NH^+$, $(C_{1-6}\ \text{alkyl})_3NH^+$, $(C_{12-18}\ \text{alkyl})_3NH^+$, or $(C_{16-18}\ \text{alkyl})_3NH^+$. The cation can be $(C_{1-3}\ \text{alkyl})_x(C_{6-12}\ \text{alkyl})_yN^+$ or $(C_{1-2}\ \text{alkyl})_x(C_{6-8}\ \text{alkyl})_yN^+$, wherein subscript x and subscript y are each 0, 1, 2, 3, or 4, and the sum of x and y is 4. The cation can be $(C_{1-8}\text{ alkyl})_z$ imidazolium, $(C_{1-6}\text{ alkyl})_z$ imidazolium, $(C_{1-8}\text{ alkyl})_z$ pyrazolium, or $(C_{1-6}\text{ alkyl})_z$ pyrazolium, wherein each subscript z is 1, 2, or 3.

In some embodiments, the cation is selected from 1-ethyl-3-methylimidazolium, 1-butyl-3-methylimidazolium, 1-ethyl-2,3-dimethylimidazolium, tris(2-hydroxyethyl) methylammonium, 1-methylimidazolium, 1,2,4-trimethylpyrazolium, triethylammonium, tributylmethylammonium, hexadecyltrimethylammonium, myristyltrimethylammonium, tridodecylmethylammonium, trimethyloctadecylammonium, and choline. In some embodiments, the cation is choline.

In certain embodiments, the ionic liquid is cholinium acetate, also referred to as [Ch][OAc], cholinium lysinate, also referred to as [Ch][Lys], or choline aspartate, also referred to as [Ch]$_2$[Asp], or a mixture thereof.

The ionic liquids used in the methods of the invention can be prepared by combining an anion, or a salt thereof, with a salt containing the cation to be incorporated into the ionic liquid. The anion and the cation can be combined as solutions in water or in a suitable organic solvent. As a non-limiting example, one equivalent of aspartic acid in aqueous solution can be combined with two equivalents of choline hydroxide in aqueous solution. Water can be removed at elevated temperature and/or under reduced pressure. Water-miscible co-solvents, including but not limited to methanol, acetonitrile, acetone, and the like, can be used to precipitate excess anions or cations for removal by centrifugation or filtration. Impurities can be removed by passing the ionic liquid through activated charcoal, polymeric ion-exchange resins, or other decolorizing agents.

In general, the molar ratio of the anions in the ionic liquid solution to the cations in the ionic liquid solution will be sufficient to provide a solution pH of at least about 7. In certain embodiments, the molar ratio of the anion to the cation is at least about 1:2 or about 1:1. The molar ratio of the dicarboxylic acid anion to the cation can be, for example, at least 1:1.8, or at least 1:1.9; or at least 1:2, or at least 1:2.1 or at least 1:2.2. When the mixture of the anion and the salt is made in aqueous solution, the pH of the resulting ionic liquid solution will be basic. In general, the pH of the ionic liquid solution is above 7. The pH of the ionic liquid solution can be, for example, at least 7, at least 7.5, at least 8, at least 8.5, at least 9, at least 9.5, at least 10, at least 10.5, at least 11, at least 11.5, at least 12, or at least 12.5. In certain embodiments, one equivalent of an anion is combined with one equivalent of a salt containing a cation and a basic anion. As a non-limiting example, combination of one equivalent of lysinate with one equivalent of choline hydroxide in aqueous solution will result in an ionic liquid solution having a pH of greater than 7. One of skill in the art will appreciate that the pH of the ionic liquid solution will vary depending on the particular anion and cation used, the ratio of the anion and the cation, and their absolute concentrations.

As described in more detail below, the pH of mixture containing the ionic liquid solution can be reduced after the pretreatment step so that mixture is compatible with enzymes, such as cellulases, used to break down the pre-treated biomass. In certain embodiments, the pH is reduced by adding the same anion that is present in the ionic liquid. Accordingly, in some embodiments an ionic liquid solution having a pH of at least about 10 is obtained by combining one equivalent of an anion with two equivalents of a salt containing a cation; the pH of the ionic liquid solution is then reduced to below about 7 via addition of a second equivalent of the anion prior to the introduction of enzymes such as glycoside hydrolases.

In certain embodiments of the invention, aqueous solutions comprising an ionic liquid or a mixture of ionic liquids are provided herein. Such solutions can be useful for, e.g., combining with a biomass to form a pre-treatment mixture, combining with a glycoside hydrolase to form a hydrolysate mixture or a sugar composition, or combining with a fermentation organism to form a fermentation product mixture. Aqueous solutions containing one or more ionic liquids can be comprise about 90%, or 80%, or 70%, or 60%, or 50%, or 40%, or 30%, or 20% or 10%, or 5%, or 1% of the ionic liquid or a mixture of ionic liquids in water. In certain embodiments, the aqueous solution comprising an ionic liquid or a mixture of ionic liquids contains about 5% to about 50% of the ionic liquid or a mixture of ionic liquids. In other embodiments, the aqueous solution comprising an ionic liquid or a mixture of ionic liquids can contain about 5% to about 40%, or about 5% to about 30%, or about 5% to about 20%, or about 5% to about 15%, or about 5% to about 10% of the ionic liquid or a mixture of ionic liquids.

Pre-Treatment Mixture Compositions

The pre-treatment mixture comprising the biomass can contain a high loading of biomass solids. For example, the pre-treatment mixture can contain up to about 50% (w/w) biomass. The pre-treatment mixture can contain, for example, from about 0.1% (w/w) to about 50% biomass, or from about 5% (w/w) to about 50% (w/w) biomass, or from about 5% (w/w) to about 20% (w/w) biomass, or from about 5% (w/w) to about 10% (w/w) biomass, or from about 10% (w/w) to about 50% (w/w) biomass, or from about 10% (w/w) to about 45% (w/w) biomass, or from about 10% (w/w) to about 35% (w/w) biomass, or from about 15% (w/w) to about 40% (w/w) biomass, or from about 15% (w/w) to about 35% (w/w) biomass, or from about 15% (w/w) to about 30% (w/w) biomass, or from about 20% (w/w) to about 35% (w/w) biomass, or from about 20% (w/w) to about 30% (w/w) biomass, or from about 30% (w/w) to about 35% (w/w) biomass by weight of the pre-treatment mixture. The pre-treatment mixture can contain about 1, 5, 10, 15, 20, 25, 30, 35, 40, 45, or 50% (w/w) biomass. In some embodiments, the pre-treatment mixture includes from about 30% (w/w) to about 40% (w/w) polysaccharide biomass. Other amounts of pre-treatment biomass can be used in the methods of the invention, depending in part on factors such as the type of biomass material and the particular ionic liquid used in the method.

The pre-treatment mixtures containing the biomass described herein typically also contain ionic liquids or a mixture of ionic liquids. Similarly, the sugar compositions, and/or fermentation product mixtures can contain ionic liquids or a mixture of ionic liquids. Such mixtures described herein can contain 30% (w/w) to about 1% (w/w) of ionic liquids or a mixture of ionic liquids. Such mixtures comprising ionic liquids or a mixture of ionic liquids described herein can be at a concentration from about 25% (w/w) to about 1% (w/w), or from about 20% (w/w) to about 1% (w/w), or from about 15% (w/w) to about 1% (w/w), or from about 10% (w/w) to about 1% (w/w), or from about 5% (w/w) to about 1% (w/w). Such mixtures comprising ionic liquids or a mixture of ionic liquids described herein can be at a concentration from about 2% (w/w) to about 30% (w/w), or from about 2% (w/w) to about 25% (w/w), or from about 2% (w/w) to about 20% (w/w), or from about 2% (w/w) to about 15% (w/w), or from about 2% (w/w) to about 10% (w/w). Such mixtures comprising ionic liquids or a mixture of ionic liquids described herein can be at a concentration of from about 5% (w/w) to about 30% (w/w), 5% (w/w) to about 25% (w/w), or from about 5% (w/w) to about 20% (w/w), or from about 5% (w/w) to about 15% (w/w), or from about 7% (w/w) to about 20% (w/w), or from about 8% (w/w) to about 15% (w/w) of ionic liquids or a mixture of ionic liquids.

The pre-treatment mixtures containing the biomass described herein typically comprise a mass ratio ($R_{m/i}$) of the biomass to the ionic liquid of the pre-treatment mixture of at least about 0.2. The $R_{m/i}$ of the biomass:ionic liquid of the pre-treatment mixture can be, for example, at least 0.18, or at least 0.19, or at least 0.2, or at least 0.21, or at least 0.22, or at least 0.23. The $R_{m/i}$ of the biomass:ionic liquid of the pre-treatment mixture can be from about 0.2 to about 7, or from about 0.2 to about 6, or from about 0.2 to about 5, or from about 0.3 to about 5, or from about 0.3 to about 4, or from about 0.3 to about 3, or from about 0.4 to about 4, or from about 0.5 to about 4, or from about 0.5 to about 3, or from about 0.6 to about 3, or from about 0.6 to about 2, or from about 0.6 to about 1, or from about 0.7 to about 1, or from about 0.8 to about 1.

Mixtures (e.g., pre-treatment mixtures, sugar compositions, fermentation product mixtures, or combinations thereof) described herein can contain a suitable amount of water. In general, the mixtures described herein can contain from about 70% (w/w) to about 95% (w/w) water. The mixtures can contain from about 70% (w/w) to about 75% (w/w) water, or from about 50% (w/w) to about 70% (w/w) water, or from about 50% (w/w) to about 75% (w/w) water, or from about 50% (w/w) to about 80% (w/w) water or from about 50% (w/w) to about 85% (w/w) water, or from about 50% (w/w) to about 90% (w/w) water, or from about 60% (w/w) to about 70% (w/w) water, or from about 60% (w/w) to about 75% (w/w) water, or from about 60% (w/w) to about 80% (w/w) water, or from about 60% (w/w) to about 85% (w/w) water, or from about 60% (w/w) to about 90% (w/w) water. The mixtures can contain from about 70% (w/w) to about 90% (w/w) water, or from about 72% (w/w) to about 85% (w/w) water, or from about 73% (w/w) to about 80% (w/w) water. The mixtures can contain from about 70% (w/w) to about 95% (w/w) water, or from about 80% (w/w) to about 93% (w/w) water, or from about 85% (w/w) to about 92% (w/w) water.

In some embodiments, the ionic liquid or mixture of ionic liquids of the pre-treatment mixture, sugar composition, fermentation product mixture, or combination thereof can be at a concentration of from about 30% (w/w) to about 5% (w/w). The ionic liquid or mixture of ionic liquids of the mixture can be at a concentration from about 25% (w/w) to about 30% (w/w), or from about 20% (w/w) to about 25% (w/w), or from about 15% (w/w) to about 20% (w/w), or from about 10% (w/w) to about 15% (w/w), or from about 5% (w/w) to about 10% (w/w). The ionic liquid or mixture of ionic liquids of the mixture can be at a concentration from about 10% (w/w) to about 30% (w/w), or from about 15% (w/w) to about 28% (w/w), or from about 20% (w/w) to about 27% (w/w). The ionic liquid or mixture of ionic liquids of the mixture can be at a concentration from about 5% (w/w) to about 30% (w/w), 5% (w/w) to about 25% (w/w), or from about 7% (w/w) to about 20% (w/w), or from about 8% (w/w) to about 15% (w/w).

IV. Methods

General

The methods of the invention are used for the production of fermentation products and intermediate products therein. In certain embodiments, a method of the invention can include:
  (i) providing a pre-treatment mixture comprising the biomass at a concentration of at least about 5% (w/w) and less than about 50%, an ionic liquid or mixture of ionic liquids at a concentration of between about 5% (w/w) and about 25% (w/w), and water, wherein the ionic liquid and biomass are present in the pre-treatment mixture at a mass ratio $R_{m/i}$ of from about 0.2 to about 5, and wherein the ionic liquid or mixture thereof comprises:
    a) a choline cation; and
    b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion;
  (ii) maintaining the mixture under pre-treatment conditions sufficient to dissolve at least a portion of the polysaccharide present in the biomass, wherein the pre-treatment conditions comprise a temperature of at least about 100° C. and less than about 200° C. for a duration of at least about 0.5 h, thereby forming a mixture comprising pre-treated biomass and the ionic liquid or mixture of ionic liquids;
  (iii) adding to the mixture comprising the pre-treated biomass and the ionic liquid or mixture of ionic liquids, a glycoside hydrolase and water under conditions sufficient to hydrolyze at least a portion of the polysaccharide present in the pre-treated biomass, thereby forming a mixture comprising a sugar composition and the ionic liquid or mixture of ionic liquids, wherein the sugar composition comprises at least one monosaccharide or oligosaccharide; and
  (iv) fermenting the mixture comprising the sugar composition and the ionic liquid or mixture of ionic liquids with a fermentation microorganism under conditions suitable to produce the fermentation product,
wherein at least 70% of glucan and/or xylan present in the biomass is converted into the fermentation product Pre-Treatment Mixtures The provided pre-treatment mixture comprising the biomass can contain a high loading of biomass solids. For example, the pre-treatment mixture can contain up to about 50% (w/w) biomass. The pre-treatment mixture can contain, for example, from about 0.1% (w/w) to about 50% biomass, or from about 5% (w/w) to about 50% (w/w) biomass, or from about 5% (w/w) to about 20% (w/w) biomass, or from about 5% (w/w) to about 10% (w/w) biomass, or from about 10% (w/w) to about 50% (w/w) biomass, or from about 10% (w/w) to about 45% (w/w) biomass, or from about 10% (w/w) to about 35% (w/w) biomass, or from about 15% (w/w) to about 40% (w/w) biomass, or from about 15% (w/w) to about 35% (w/w) biomass, or from about 15% (w/w) to about 30% (w/w) biomass, or from about 20% (w/w) to about 35% (w/w) biomass, or from about 20% (w/w) to about 30% (w/w) biomass, or from about 30% (w/w) to about 35% (w/w) biomass by weight of the pre-treatment mixture. The pre-treatment mixture can contain about 1, 5, 10, 15, 20, 25, 30, 35, 40, 45, or 50% (w/w) biomass. In some embodiments, the pre-treatment mixture includes from about 30% (w/w) to about 40% (w/w) polysaccharide biomass. Other amounts of pre-treatment biomass can be used in the methods of the invention, depending in part on factors such as the type of biomass material and the particular ionic liquid used in the method.

The pre-treatment mixture can be provided by combining in a reaction chamber a biomass, one or more ionic liquids, and water. The combining can be done separately or sequentially. In certain embodiments, water is added first, and to water is added ionic liquid, and biomass is added to an aqueous ionic liquid solution. In some embodiments, water and biomass are combined and ionic liquid(s) are added to a biomass slurry. One of skill in the art will understand that other orders of addition are suitable.

The provided pre-treatment biomass mixture can contain a suitable amount of water. The pre-treatment biomass mixture containing an amount of water can also contain an ionic liquid or a mixture of ionic liquids at concentrations disclosed herein. In general, the provided pre-treatment biomass mixture herein contains from about 70% (w/w) to about 95% (w/w) water. The provided pre-treatment biomass mixture can contain from about 70% (w/w) to about 75% (w/w) water, or from about 50% (w/w) to about 70% (w/w) water, or from about 50% (w/w) to about 75% (w/w) water, or from about 50% (w/w) to about 80% (w/w) water or from about 50% (w/w) to about 85% (w/w) water, or from about 50% (w/w) to about 90% (w/w) water, or from about 60% (w/w) to about 70% (w/w) water, or from about 60% (w/w) to about 75% (w/w) water, or from about 60% (w/w) to about 80% (w/w) water, or from about 60% (w/w) to about 85% (w/w) water, or from about 60% (w/w) to about 90% (w/w) water. The provided pre-treatment biomass mixture can contain from about 70% (w/w) to about 90% (w/w) water, or from about 72% (w/w) to about 85% (w/w) water, or from about 73% (w/w) to about 80% (w/w) water. The provided pre-treatment biomass mixture can contain from about 70% (w/w) to about 95% (w/w) water, or from about 80% (w/w) to about 93% (w/w) water, or from about 85% (w/w) to about 92% (w/w) water.

In some embodiments, the ionic liquid or mixture of ionic liquids of the pre-treatment mixture can be at a concentration of from about 30% (w/w) to about 5% (w/w). The ionic liquid or mixture of ionic liquids of the pre-treatment mixture can be at a concentration from about 25% (w/w) to about 30% (w/w), or from about 20% (w/w) to about 25% (w/w), or from about 15% (w/w) to about 20% (w/w), or from about 10% (w/w) to about 15% (w/w), or from about 5% (w/w) to about 10% (w/w). The ionic liquid or mixture of ionic liquids of the pre-treatment mixture can be at a concentration from about 10% (w/w) to about 30% (w/w), or from about 15% (w/w) to about 28% (w/w), or from about 20% (w/w) to about 27% (w/w). The ionic liquid or mixture of ionic liquids of the pre-treatment mixture can be at a concentration from about 5% (w/w) to about 30% (w/w), 5% (w/w) to about 25% (w/w), or from about 7% (w/w) to about 20% (w/w), or from about 8% (w/w) to about 15% (w/w).

In general, the mass ratio ($R_{m/i}$) of the biomass to the ionic liquid of the pre-treatment mixture is at least about 0.2. The $R_{m/i}$ of the biomass:ionic liquid of the pre-treatment mixture can be, for example, at least 0.18, or at least 0.19, or at least 0.2, or at least 0.21, or at least 0.22, or at least 0.23. The $R_{m/i}$ of the biomass:ionic liquid of the pre-treatment mixture can be from about 0.2 to about 7, or from about 0.2 to about 6, or from about 0.2 to about 5, or from about 0.3 to about 5, or from about 0.3 to about 4, or from about 0.3 to about 3, or from about 0.4 to about 4, or from about 0.5 to about 4, or from about 0.5 to about 3, or from about 0.6 to about 3, or from about 0.6 to about 2, or from about 0.6 to about 1, or from about 0.7 to about 1, or from about 0.8 to about 1.

Pre-Treatment Conditions

In certain embodiments, the pre-treatment conditions of the method step (ii) as described above can be maintained for a suitable length of time at a suitable temperature and pressure to achieve adequate pre-treatment. The degree of pre-treatment and its suitability for hydrolysis can be assessed by methods described herein including, but not limited to performing composition analysis of the pre-treated biomass to measure lignin and/or hemicellulose removal, or retention of cellulose, or a combination thereof. The degree of pre-treatment and its suitability for hydrolysis can be assessed by methods described herein including, but not limited to powder diffraction analysis of extracted cellulose. The degree of pre-treatment and its suitability for hydrolysis can be assessed by methods described herein including, but not limited to, performing hydrolysis with a glycoside hydrolase and measuring hydrolysis efficacy with High Performance Liquid Chromatography (HPLC) to assess the degree of lignocellulose removal. The degree of saccharification of method step (iii) and its suitability for fermentation can be assessed by methods described herein including, but not limited to, measuring the efficacy with HPLC to assess the sugar composition yield. The degree of fermentation of method step (iv) and its production of a fermentation product can be assessed by methods described herein including, but not limited to, measuring the efficacy of fermentation with HPLC and a compositional analysis to assess the degree of sugar to ethanol conversion.

In general, pre-treatment is conducted for anywhere from a few minutes to several hours. Pre-treatment can be conducted, for example, for about five minutes, or about 10 minutes, or about 30 minutes, or about 60 minutes, or about 90 minutes, or about 120 minutes, or about 150 minutes, or about 180 minutes. Pre-treatment can be conducted for about 1, 1.5, 2, 2.5, 3, 3.5, 4, 4.5, 5, 5.5, 6, 9, 12, 15, 18, 21, 24, 36, 48, 60, or about 72 hours. Pre-treatment is generally conducted at a temperature ranging from about 20° C. to about 200° C. Pre-treatment can be conducted, for example, at a temperature ranging from about 20° C. to about 100° C., or from about 40° C. to about 80° C., or from about 100° C. to about 200° C., or from about 120° C. to about 180° C., or from about 140° C. to about 160° C., or from about 40° C. to about 180° C., or from about 60° C. to about 160° C., or from about 80° C. to about 140° C., or from about 100 to about 120° C. Pre-treatment can be conducted at about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or about 200° C. for at least about 0.5, 1, 3, 6, 9, 12, or 16 hours. Pre-treatment can be conducted at atmospheric pressure or elevated pressures. Pre-treatment can be conducted, for example, at a pressure (Pg) ranging from about 14 psi to about 4000 psi, or from about 14 psi to about 3500 psi, or from about 14 psi to about 2500 psi, or from about 14 psi to about 1500 psi, or from about 14 psi to about 1000 psi, or from about 14 psi to about 500 psi, or from about 14 psi to about 400 psi, or from about 14 psi to about 300 psi, or from about 14 psi to about 200 psi, or from about 14 psi to about 100 psi, or from about 14 psi to about 50 psi, or from about 14 psi to about 30 psi, or from about 14 psi to about 20 psi. In certain embodiments, the pre-treatment is conducted at around atmospheric pressure (i.e., 14.696 psi).

In general, the pH of the pre-treatment mixture is at or above 7. The pH of the pre-treatment mixture can be, for example, at least 7, at least 7.5, at least 8, at least 8.5, at least 9, at least 9.5, at least 10, at least 10.5, at least 11, at least 11.5, at least 12, or at least 12.5. One of skill in the art will appreciate that the pH of the pre-treatment mixture will vary depending on the particular anion and cation used, the ratio of the anion and the cation, and their absolute concentrations.

Saccharification

Following pre-treatment of the polysaccharide biomass, the pH of the mixture containing the dissolved polysaccharide and the ionic liquid solution can be reduced to a level that is suitable for enzymatic hydrolysis of the polysaccharide by one or more glycoside hydrolases. In general, the pH of mixture is reduced to at most about 7. The pH of the mixture can be reduced, for example, to less than 7, at or about 6.5, at or about 6, at or about 5.5, at or about 5, at or about 4.5, or at or about 4.0. In certain embodiments, the pH of the mixture is reduced to a pH of from about 4 to about 6, or from about 4.5 to about 6.5, or from about 4.8 to about 6.2, or from about 4.8 to about 5.2, or from about 5.2 to about 6.5, or from about 5.2 to about 6.2. The pH of the mixture containing the dissolved polysaccharide can be reduced by adding an acid to the mixture. Any suitable acid can be used to reduce the pH. Suitable acids include, but are not limited to, hydrochloric acid, sulfuric acid, nitric acid, acetic acid, citric acid, formic acid, and the like. One of skill in the art will appreciate that the pH of the mixture containing the dissolved polysaccharide can be adjusted to maximize the activity of an enzyme, or a mixture of enzymes, e.g., one or more glycoside hydrolases, used in the subsequent hydrolysis step. The particular pH will depend in part on factors including, but not limited to, the specific glycoside hydrolase(s) and the amount of ionic liquid in the mixture.

The methods of the invention generally include adding on or more enzymes that break down polysaccharide biomass into smaller components. Typically, the pre-treated biomass is subjected to the action of one, or multiple, enzyme activities selected from a protease, a lipase, a cellulase, an amylase, a glucano-hydrolase, a pectinase, a xylanase, a ferulic acid esterase, and a mannanase. The pre-treated biomass may also be treated with other enzymes, e.g., hemicellulases, that are used for the degradation of biomass.

In some embodiments, the glycoside hydrolase is selected from an endoglucanase, an exoglucanase, a β-glucosidase, a xylanase, and mixtures thereof. In some embodiments, one or more cellulases are added to the pre-treated biomass present in the ionic liquid mixture in which the pH has been reduced, e.g., to about 7, following treatment at a high pH.

A "cellulase" as used herein is a glycoside hydrolase enzyme that hydrolyzes cellulose (β-1,4-glucan or β-D-glucosidic linkages) resulting in the formation of glucose, cellobiose, cellooligosaccharides, and the like. In the context of the present invention, cellulases include endoglucanases; exoglucanases or cellobiohydrolases; and 3-glucosidases. Endoglucanases (EC 3.2.1.4) including endo-1,4-β-glucanases or 1,4-β-D-glucan-4-glucanohydrolases, act randomly on soluble and insoluble 1,4-β-glucan substrates. Exoglucanases (exo-1,4-β-D-glucanases, e.g., the 1,4-β-D-glucan glucohydrolases; EC 3.2.1.74) liberate D-glucose from 1,4-β-D-glucans and hydrolyze D-cellobiose slowly. Cellobiohydrolases (1,4-β-D-glucan cellobiohydrolases, EC 3.2.1.91) liberate D-cellobiose from 1,413-glucans. β-Glucosidases ([β]-D-glucoside glucohydrolase; β-D-glucosidases; EC 3.2.1.21) act to release D-glucose units from cellobiose and soluble cellodextrins, as well as an array of glycosides. Endoglucanases act mainly on the amorphous parts of the cellulose fiber, whereas cellobiohydrolases are also able to degrade crystalline cellulose.

A combination of two or more cellulases can be used in the methods of the invention. Cellulases act in concert to catalyze the hydrolysis of cellulose-containing substrates. For example, endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. β-glucosidases split the cellobiose into glucose monomers. The cellulase can be a thermostable cellulase. In certain embodiments the glycoside hydrolase, such as a cellulase, is selected such that it can perform optimally in the presence of ionic liquid.

A xylanase and/or a "mannanase" may also be employed in the saccharification of pre-treated biomass. A "xylanase" is a glycoside hydrolase enzyme that catalyzes the endo-hydrolysis of 1,4-β-D-xylosidic linkages in xylans. Xylanases include enzymes classified as a 1,4-β-D-xylan-xylohydrolase (E. C. 3.2.1.8).

A "mannanase" is a glycoside hydrolase that hydrolyzes 1,4-β-D-mannosidic linkages in mannans, galactomannans and/or glucomannans. "Mannanase activity" refers to hydrolysis of 1,4-β-D-mannosidic linkages in mannans, galactomannans and/or glucomannans. Mannases include enzymes classified as EC 3.2.1.78.

A suitable amount of enzyme or enzyme mixture, e.g., glycoside hydrolase or mixture of glycoside hydrolases, can be used in the methods of the invention. In general a sub-stoichiometric amount of the glycoside hydrolase, with respect to the dissolved polysaccharide, is used. The amount of glycoside hydrolase can be expressed as activity units. Alternatively, the amount of the glycoside hydrolase used in the methods of the invention can be expressed relative to the amount of biomass treated in the pre-treatment step. For example, the hydrolysis mixture can contain a glycoside hydrolase (or a mixture of glycoside hydrolases) in an amount ranging from about 0.01 to about 10% (w/w), with respect to the amount of biomass used in the pre-treatment step. Thus, for example, when the method is conducted using 1 kg of biomass, for example, the hydrolysis step can be conducted with a glycoside hydrolase or a mixture of glycoside hydrolases in an amount ranging from about 100 mg to about 100 g. Those of skill in the art will appreciate that the amount of glycoside hydrolase or mixture of enzymes used in the methods of the invention will depend in part on factors including, but not limited to, the particular enzyme used, the nature of the biomass source, and the extent of the pre-treatment step.

The step (iii) of the methods herein involving enzymatic hydrolysis can be conducted for a length of time at a suitable temperature. The enzymatic hydrolysis step can be conducted, for example, for about 2, 5, 10, 15, 30, 45, or 60 minutes. The enzymatic hydrolysis step can be conducted for about 1, 1.5, 2, 2.5, 3, 3.5, 4, 4.5, 5, 5.5, 6, 9, 12, 15, 18, 21, 24, 30, 36, 42, 48, or 72 hours. In certain embodiments, the mixture of step (iii) can be maintained under conditions sufficient to produce a mixture comprising at least a portion of the hydrolyzed polysaccharide for at least 1 day to at least 12 days. In some cases, the mixture of step (iii) is maintained under conditions sufficient to hydrolyze the polysaccharide present in the mixture for at least 1 day to at least 10 days, or at least 2 days to at least 9 days, or at least 3 days to at least 8 days, or at least 4 days to at least 7 days, or at least 5 days to at least 6 days. In certain embodiments, the mixture of step (iii) is maintained under conditions sufficient to hydrolyze the polysaccharide present in the mixture for at least 2 days, or at least 2 to at least 8 days, or at least 2 days to at least 10 days, or at least 3 days to at least 9 days.

Enzymatic hydrolysis is generally conducted at a temperature ranging from about 20° C. to about 60° C. Enzymatic hydrolysis can be conducted, for example, at a temperature ranging from about 20° C. to about 40° C., or from about 40° C. to about 60° C., or from about 30° C. to about 55° C., or from about 40° C. to about 55° C., or from about 40° C. to about 50° C., or from about 37° C. to about 55° C., or from about 35° C. to about 55° C. Enzymatic hydrolysis can be conducted at about 25° C., about 37° C., or about 55° C. for at least about 10, 20, 30, 60, or 90 minutes or for at least about 2, 3, 4, 5, 6, 7, 8, 9, 10, 11, 12, 24, 48, or 72 hours.

In certain embodiments, the saccharification is performed under conditions sufficient to produce a sugar titer of from about 25 g/L to about 150 g/L, from about 30 g/L to about 100 g/L, from about 30 g/L to about 90 g/L, from about 40 g/L to about 85 g/L, or about 60, 70, or 80 g/L. In certain embodiments, the saccharification is performed under conditions sufficient to produce a sugar titer of from about 30 g/L to about 100 g/L, from about 40 g/L to about 95 g/L, from about 45 g/L to about 90 g/L, or from about 50 g/L to about 85 g/L.

In certain embodiments, saccharification is conducted without removing the ionic liquid from the pre-treatment mixture. In some cases, saccharification is conducted without removing more than about 50%, or 40%, or 30%, or 20% or 10%, or 5%, or 1% of the ionic liquid from the pre-treatment mixture. In certain embodiments, the fermentation mixture contains at about 50% to about 99% of the ionic liquid present in the pre-treatment mixture. The fermentation mixture can contain about 50% to about 95%, or about 50% to about 90%, or about 55% to about 85%, or about 60% to about 80%, or about 65% to about 75% of the ionic liquid present in the pre-treatment mixture. In some embodiments, the saccharification is conducted in the mixture containing the ionic liquid and the pre-treated biomass resulting from one or more pre-treatment methods described above. In some embodiments, saccharification can comprise adding a glycoside hydrolase to the mixture containing the pre-treated biomass and the ionic liquid or mixture of ionic liquids.

Fed Batch Saccharification

In certain embodiments of the invention, the methods described herein may be performed via batchwise or fed-batch steps to produce a polysaccharide hydrolysate for fermentation, wherein a biomass slurry (e.g., pre-treated biomass slurry, or pre-treated and at least partially hydrolyzed biomass slurry) is loaded into a hydrolysis mixture, as described below. Typically, the hydrolysis mixture is performed under conditions described above in combination with periodic addition of pre-treated biomass to the hydrolysis reaction, and additional or alternative parameters are described below.

In some aspects of the invention, the method of producing a polysaccharide hydrolysate from biomass, wherein the biomass comprises polysaccharide and lignin. In one aspect, the method comprises:
  (i) providing a slurry comprising pre-treated biomass at a concentration of at least about 5% (w/w) and less than about 50% (w/w), an ionic liquid or mixture of ionic liquids at a concentration of between about 5% (w/w) and about 25% (w/w), and water, wherein the ionic liquid and biomass are present in the pre-treated slurry at a mass ratio $R_{m/i}$, of from about 0.2 to about 5, and wherein the ionic liquid or mixture thereof comprises:
    a) a choline cation; and
    b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion, wherein the mixture optionally comprises a glycoside hydrolase;
  (ii) introducing a portion of the pre-treated biomass slurry to a mixture comprising water and optionally the glycoside hydrolase, thereby forming a mixture comprising a portion of the pre-treated biomass slurry, the glycoside hydrolase, and water;
  (iii) maintaining the mixture comprising a portion of the pre-treated biomass slurry, the glycoside hydrolase, and water under conditions sufficient to hydrolyze the polysaccharide present in the portion of the pre-treated biomass, thereby forming a mixture comprising a hydrolyzed polysaccharide;
  (iv) adding to the mixture comprising the hydrolyzed polysaccharide an additional portion of the pre-treated biomass slurry of step (i), and maintaining the mixture comprising the hydrolyzed polysaccharide under conditions sufficient to hydrolyze the polysaccharide present in the mixture; and
  (v) optionally repeating the step of (iv) 1 to 100 times, wherein at least 70% of glucan and/or xylan present in the biomass is converted into a monosaccharide.

Another aspect of the present invention provides a method of producing a polysaccharide hydrolysate from biomass, wherein the biomass comprises polysaccharide and lignin. In one aspect, the method comprises:
  (i) providing a slurry comprising pre-treated biomass at a concentration of at least about 5% (w/w) and less than about 50% (w/w), an ionic liquid or mixture of ionic liquids at a concentration of between about 5% (w/w) and about 25% (w/w), and water, wherein the ionic liquid and biomass are present in the pre-treated slurry at a mass ratio $R_{m/i}$, of from about 0.2 to about 5, and wherein the ionic liquid or mixture thereof comprises:
    a) a choline cation; and
    b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion, wherein the mixture optionally comprises a glycoside hydrolase;
  (ii) introducing a portion of the pre-treated biomass slurry to a mixture comprising a sugar composition and optionally the glycoside hydrolase, wherein the sugar composition is at a concentration of at least 70% (w/w), thereby forming a mixture comprising a portion of the pre-treated biomass slurry, the glycoside hydrolase, and the sugar composition;
  (iii) maintaining the mixture comprising the portion of the pre-treated biomass slurry, the glycoside hydrolase, and the sugar composition under conditions sufficient to hydrolyze polysaccharide present in the portion of the pre-treated biomass, thereby forming a further mixture comprising hydrolyzed polysaccharide;
  (iv) adding to the further mixture comprising the hydrolyzed polysaccharide an additional portion of the pre-treated biomass slurry of step (i), and maintaining the further mixture comprising the hydrolyzed polysaccharide under conditions sufficient to hydrolyze the polysaccharide present in the mixture; and
  (v) optionally repeating the step of (iv) 1 to 100 times, wherein at least 70% of glucan and/or xylan present in the biomass is converted into a monosaccharide.

In certain embodiments, each step of methods described herein can be performed in a single reaction vessel or chamber. The steps of the methods can be performed consecutively or non-consecutively. In some embodiments, one or more steps are partially or completely performed simultaneously. For example, pre-treatment and hydrolysis can be performed partially or completely simultaneously. As another example, hydrolysis and fermentation can be performed partially or completely simultaneously. In some cases, hydrolysis is performed for a period of time with a glycoside hydrolase at a temperature and pH that is optimal for one or more glycoside hydrolase activities, and the further hydrolysis is performed during fermentation and in the presence of a fermentation organism at a temperature and pH that is optimal for the fermentation organism or at an intermediate temperature and/or pH that is between the optimal parameters for hydrolysis and fermentation.

Fed Batch Saccharification: Pre-Treated Biomass Slurry

In certain embodiments of the methods of the invention, the slurry comprising the pre-treated biomass can contain a high loading of biomass solids. For example, the slurry can contain up to about 50% (w/w) biomass. The slurry comprising the pre-treatment biomass can be at a concentration of, for example, from about 0.1% (w/w) to about 50% biomass solids, or from about 5% (w/w) to about 50% (w/w) biomass solids, or from about 5% (w/w) to about 20% (w/w) biomass solids, or from about 5% (w/w) to about 10% (w/w) biomass solids, or from about 10% (w/w) to about 50% (w/w) biomass solids, or from about 10% (w/w) to about 45% (w/w) biomass solids, or from about 10% (w/w) to about 35% (w/w) biomass solids, or from about 15% (w/w) to about 40% (w/w) biomass solids, or from about 15% (w/w) to about 35% (w/w) biomass solids, or from about 15% (w/w) to about 30% (w/w) biomass solids, or from about 20% (w/w) to about 35% (w/w) biomass solids, or from about 20% (w/w) to about 30% (w/w) biomass solids, or from about 30% (w/w) to about 35% (w/w) biomass solids by weight of the slurry. The slurry comprising pre-treated biomass can contain about 1, 5, 10, 15, 20, 25, 30, 35, 40, 45, or 50% (w/w) biomass solids. In some embodiments, the biomass slurry includes from about 30% (w/w) to about 40% (w/w) biomass solids. Other amounts of pre-treatment biomass solids in the slurry can be used in the methods of the invention, depending in part on factors such as the type of biomass material and the particular ionic liquid used in the method.

In certain embodiments of the methods of the invention, the slurry comprising the pre-treated biomass and the ionic liquid or mixture of ionic liquids can contain up to about 30% (w/w) to about 1% (w/w) of ionic liquids or a mixture of ionic liquids. Such slurries comprising ionic liquids or a mixture of ionic liquids described herein can be at a concentration from about 25% (w/w) to about 1% (w/w), or from about 20% (w/w) to about 1% (w/w), or from about 15% (w/w) to about 1% (w/w), or from about 10% (w/w) to about 1% (w/w), or from about 5% (w/w) to about 1% (w/w) of ionic liquids or a mixture of ionic liquids. Such slurries comprised of ionic liquids or a mixture of ionic liquids described herein can be at a concentration from about 2% (w/w) to about 30% (w/w), or from about 2% (w/w) to about 25% (w/w), or from about 2% (w/w) to about 20% (w/w), or from about 2% (w/w) to about 15% (w/w), or from about 2% (w/w) to about 10% (w/w) ionic liquids or a mixture of ionic liquids. Such slurries comprised of ionic liquids or a mixture of ionic liquids described herein can be at a concentration from about 5% (w/w) to about 30% (w/w), 5% (w/w) to about 25% (w/w), or from about 5% (w/w) to about 20% (w/w), or from about 5% (w/w) to about 15% (w/w), or from about 7% (w/w) to about 20% (w/w), or from about 8% (w/w) to about 15% (w/w) of ionic liquids or a mixture of ionic liquids.

In some embodiments of the methods of the invention, the ionic liquid or mixture of ionic liquids and the biomass are present in the pre-treated slurry at a mass ratio ($R_{m/i}$) of the biomass to the ionic liquid of the pre-treated slurry of at least about 0.2. The $R_{m/i}$ of the biomass:ionic liquid of the pre-treated slurry can be, for example, at least 0.18, or at least 0.19, or at least 0.2, or at least 0.21, or at least 0.22, or at least 0.23. The $R_{m/i}$ of the biomass:ionic liquid of the pre-treated slurry can be from about 0.2 to about 7, or from about 0.2 to about 6, or from about 0.2 to about 5, or from about 0.3 to about 5, or from about 0.3 to about 4, or from about 0.3 to about 3, or from about 0.4 to about 4, or from about 0.5 to about 4, or from about 0.5 to about 3, or from about 0.6 to about 3, or from about 0.6 to about 2, or from about 0.6 to about 1, or from about 0.7 to about 1, or from about 0.8 to about 1.

Fed Batch Saccharification: Mixtures of Glycoside Hydrolase

In some embodiments of the invention, the pre-treated biomass slurry of the methods optionally comprises a glycoside hydrolase. The pre-treated biomass slurry of the methods will contain a glycoside hydrolase in cases where the mixture of step (ii) of the methods of producing a polysaccharide hydrolysate does not contain a glycoside hydrolase. The pre-treated biomass slurry of the methods can contain a glycoside hydrolase in cases where the mixture of step (ii) of the methods of producing a polysaccharide hydrolysate does contain a glycoside hydrolase. In certain embodiments, the method of step (ii) comprises introducing a portion of the pre-treated biomass slurry to a mixture of step (ii). In other embodiments, the mixture of step (ii) can be introduced to a portion of biomass slurry.

In some embodiments, step (ii) of the methods of producing a polysaccharide hydrolysate from biomass involves introducing a portion of the pre-treated biomass slurry to a mixture comprising water and optionally a glycoside hydrolase. Accordingly, in some embodiments the portion of the pre-treated biomass slurry is introduced to any suitable amount of water. For example, the portion of the pre-treated biomass slurry can be introduced to water in a proportion corresponding to about a 0.3 g, or 3 g, or 10 g, or 30 g portion of pre-treated biomass slurry into from about 0.1 milliliter to about 1000 milliliters of water, or from about 1 milliliter to about 750 milliliters of water, or from about 2 milliliters to about 500 milliliters of water, or from about 2 milliliters to about 250 milliliters of water, or from about 2 milliliter to about 100 milliliters of water, or from about 2 milliliters to about 50 milliliters of water, or from about 1 milliliter to about 25 milliliters of water, or from about 1 milliliter to about 20 milliliters of water, or from about 1 milliliter to about 10 milliliters of water. In some embodiments, the portion of the pre-treated biomass slurry can be introduced to water in a proportion corresponding to about a 0.3 g, or 3 g, or 10 g, or 30 g portion of pre-treated biomass slurry in from about 0.1 milliliter to about 10 milliliters of water, or from about 0.5 milliliter to about 8 milliliters of water, or from about 1 milliliter to about 7 milliliters of water, or from about 2 milliliters to about 6 milliliters of water, or from about 2 milliliters to about 5 milliliters of water. In some cases, the portion of the pre-treated biomass slurry can be introduced to water in a proportion corresponding to about a 0.3 g, or 3 g, or 10 g, or 30 g portion of pre-treated biomass slurry in about 0.1, 1, 2, 3, 4, 5, 6, 7, 8, 9, or 10 milliliters of water.

The method of introducing a portion of the pre-treated biomass slurry of step (ii) to a mixture comprising water and optionally the glycoside hydrolase can involve the introduction of the portion of biomass slurry at a rate from at least 1 gram per day to about 35 grams per day per about 10 to 200 milliliters of the mixture comprising the portion of the pre-treated biomass slurry, the glycoside hydrolase, and water.

In some embodiments of step (ii), introducing a portion of the pre-treated biomass slurry to a mixture comprising water and optionally the glycoside hydrolase can involve the introduction of the portion of biomass slurry at a rate from at least 2 grams per day to about 30 grams per day per about 15 to 150 milliliters of the mixture comprising the portion of the pre-treated biomass slurry, the glycoside hydrolase, and water, or from at least 2 grams per day to about 25 grams per day per about 20 to 100 milliliters of the mixture comprising the portion of the pre-treated biomass slurry, the glycoside hydrolase, and water, or from at least 2 grams per day to about 20 grams per day per about 20 to 50 milliliters of the mixture comprising the portion of the pre-treated biomass slurry, the glycoside hydrolase, and water, or from at least 2 grams per day to about 15 grams per day per about 20 to 30 milliliters of the mixture comprising the portion of the pre-treated biomass slurry, the glycoside hydrolase, and water, or from at least 2 grams per day to about 10 grams per day per about 10 to 25 milliliters of the mixture comprising the portion of the pre-treated biomass slurry, the glycoside hydrolase, and water.

In some embodiments of step (ii), introducing a portion of the pre-treated biomass slurry to a mixture comprising water and optionally the glycoside hydrolase can involve the introduction of the portion of biomass slurry at a rate from at least 2 grams per day to at least 20 grams per day, or 3 grams per day to about 20 grams per day, or from at least 4 grams per day to about 15 grams per day, or from about 5 grams per day to about 12 grams per day per about 30 milliliters of the mixture comprising the portion of the pre-treated biomass slurry, the glycoside hydrolase, and water.

In some cases, step (ii) of the methods of producing a polysaccharide hydrolysate from biomass involves introducing a portion of the pre-treated biomass slurry to a mixture comprising a sugar composition and optionally a glycoside hydrolase. Accordingly, in some embodiments the portion of the pre-treated biomass slurry is introduced to any suitable amount of a sugar composition. For example, the portion of the pre-treated biomass slurry can be introduced to from about 0.1 milliliter to about 1000 milliliters of sugar composition, or from about 1 milliliter to about 750 milliliters of sugar composition, or from about 2 milliliters to about 500 milliliters of sugar composition, or from about 2 milliliters to about 250 milliliters of sugar composition, or from about 2 milliliter to about 100 milliliters of sugar composition, or from about 2 milliliters to about 50 milliliters of sugar composition, or from about 1 milliliter to about 25 milliliters of sugar composition, or from about 1 milliliter to about 20 milliliters of sugar composition, or from about 1 milliliter to about 10 milliliters of sugar composition.

In some embodiments, the portion of the pre-treated biomass slurry can be introduced to from about 0.1 milliliter to about 10 milliliters of sugar composition, or from about 0.5 milliliter to about 8 milliliters of sugar composition, or from about 1 milliliter to about 7 milliliters of sugar composition, or from about 2 milliliters to about 6 milliliters of sugar composition, or from about 2 milliliters to about 5 milliliters of sugar composition. In some cases, the portion of the pre-treated biomass slurry can be introduced to about 0.1, 1, 2, 3, 4, 5, 6, 7, 8, 9, or 10 milliliters of sugar composition.

The sugar composition of step (ii) described herein is a concentrated sugar composition. Such sugar compositions described herein can be at a concentration of at least 30% (w/w) to less than about 100% (w/w) of hydrolysates. Such concentrated sugar compositions comprising hydrolysates described herein can be at a concentration of from about 45% (w/w) to less than about 100% (w/w), or from about 50% (w/w) to about 95% (w/w), or from about 65% (w/w) to about 95% (w/w), or from about 70% (w/w) to about 90% (w/w), or from about 70% (w/w) to about 100% (w/w) hydrolysates. Such concentrated sugar compositions comprising hydrolysates described herein can be at a concentration of from at least 70% (w/w), 75% (w/w), 80% (w/w), 85% (w/w), 90% (w/w), 95% (w/w), 99% (w/w), or 99% (w/w) hydrolysates.

The method of introducing a portion of the pre-treated biomass slurry of step (ii) to a mixture comprising a sugar composition and optionally the glycoside hydrolase can involve the introduction of the portion of biomass slurry at a rate from at least 1 gram per day to about 60 grams per day per about 10 to 300 milliliters of the mixture comprising the portion of the pre-treated biomass slurry, the glycoside hydrolase, and the sugar composition.

In some embodiments of step (ii), introducing a portion of the pre-treated biomass slurry to a mixture comprising the sugar composition and optionally the glycoside hydrolase can involve the introduction of the portion of biomass slurry at a rate from at least 2 grams per day to about 50 grams per day per about 15 to 250 milliliters of the mixture comprising the portion of the pre-treated biomass slurry, the glycoside hydrolase, and the sugar composition, or from at least 2 grams per day to about 45 grams per day per about 20 to 200 milliliters of the mixture comprising the portion of the pre-treated biomass slurry, the glycoside hydrolase, and the sugar composition, or from at least 2 grams per day to about 40 grams per day per about 30 to 100 milliliters of the mixture comprising the portion of the pre-treated biomass slurry, the glycoside hydrolase, and the sugar composition, or from at least 2 grams per day to about 35 grams per day per about 20 to 60 milliliters of the mixture comprising the portion of the pre-treated biomass slurry, the glycoside hydrolase, and the sugar composition, or from at least 2 grams per day to about 30 grams per day per about 10 to 40 milliliters of the mixture comprising the portion of the pre-treated biomass slurry, the glycoside hydrolase, and the sugar composition.

In some embodiments of step (ii), introducing a portion of the pre-treated biomass slurry to a mixture comprising the sugar composition and optionally the glycoside hydrolase can involve the introduction of the portion of biomass slurry at a rate from at least 2 grams per day to at least 40 grams per day, or 4 grams per day to about 30 grams per day, or from at least 5 grams per day to about 20 grams per day, or from about 6 grams per day to about 15 grams per day per about 60 milliliters of the mixture comprising the portion of the pre-treated biomass slurry, the glycoside hydrolase, and the sugar composition.

Fed Batch Saccharification: Polysaccharide Hydrolysis

In some embodiments of step (iii), the mixture comprising a portion of the pre-treated biomass slurry, the glycoside hydrolase, and water can be maintained under conditions sufficient to produce a mixture comprising a hydrolyzed polysaccharide. In other embodiments of step (iii), the mixture comprising a portion of the pre-treated biomass slurry, the glycoside hydrolase, and the sugar composition can be maintained under conditions sufficient to produce a mixture comprising a hydrolyzed polysaccharide. Such conditions for preforming enzymatic hydrolysis of a biomass have been described throughout the specification. In some embodiments, the mixture of step (iii) can be maintained under conditions sufficient to produce a mixture comprising a hydrolyzed polysaccharide for at least 1 day to at least 12 days. In some cases, step (iii), wherein the mixture comprising the portion of the pre-treated biomass slurry, the glycoside hydrolase, and either water or the sugar composition, is maintained under conditions sufficient to hydrolyze the polysaccharide present in the mixture for at least 1 day to at least 10 days, or at least 2 days to at least 9 days, or at least 3 days to at least 8 days, or at least 4 days to at least 7 days, or at least 5 days to at least 6 days. In certain embodiments, step (iii), wherein the mixture comprising the portion of the pre-treated biomass slurry, the glycoside hydrolase, and either water or the sugar composition, is maintained under conditions sufficient to hydrolyze the polysaccharide present in the mixture for at least 1 day, or at least 2 days, or at least 2 to at least 7 days, or at least 2 days to at least 5 days, or at least 2 days to at least 4 days.

In some embodiments of the methods of producing a polysaccharide hydrolysate from biomass, step (iv) involves adding to the mixture comprising the hydrolyzed polysaccharide an additional portion of the pre-treated biomass slurry of step (i). In other embodiments of the methods of producing a polysaccharide hydrolysate from biomass, step (iv) involves adding to an additional portion of pre-treated biomass slurry of step (i) the mixture comprising the hydrolyzed polysaccharide. In some embodiments, step (iv) can be repeated 1 to 100 times. The repeating of step (iv) can involve the introduction of an additional portion of the pre-treated biomass slurry of step (i) to the mixture comprising the hydrolyzed polysaccharide, or the repeating of step (iv) can involve the introduction of the mixture comprising the hydrolyzed polysaccharide to an additional portion of the pre-treated biomass slurry of step (i).

The method of adding to the mixture comprising the hydrolyzed polysaccharide and an additional portion of the pre-treated biomass slurry of step (i), and maintaining the mixture comprising the hydrolyzed polysaccharide and water under conditions sufficient to hydrolyze the polysaccharide present in the mixture can involve the introduction of the additional portion of biomass slurry at a rate from at least 1 gram per day to about 35 grams per day per about 10 to 200 milliliters of the mixture comprising the additional portion of the pre-treated biomass slurry, the hydrolyzed polysaccharide, the glycoside hydrolase, and water.

In some embodiments of step (iv), introducing an additional portion of the pre-treated biomass slurry to a mixture comprising the hydrolyzed polysaccharide and water under conditions sufficient to hydrolyze the polysaccharide present in the mixture can involve the introduction of the portion of biomass slurry at a rate from at least 2 grams per day to about 30 grams per day per about 15 to 150 milliliters of the mixture comprising the additional portion of the pre-treated biomass slurry, the hydrolyzed polysaccharide, the glycoside hydrolase, and water, or from at least 2 grams per day to about 25 grams per day per about 20 to 100 milliliters of the mixture comprising the additional portion of the pre-treated biomass slurry, the hydrolyzed polysaccharide, the glycoside hydrolase, and water, or from at least 2 grams per day to about 20 grams per day per about 20 to 50 milliliters of the mixture comprising the additional portion of the pre-treated biomass slurry, the hydrolyzed polysaccharide, the glycoside hydrolase, and water, or from at least 2 grams per day to about 15 grams per day per about 20 to 30 milliliters of the mixture comprising the additional portion of the pre-treated biomass slurry, the hydrolyzed polysaccharide, the glycoside hydrolase, and water, or from at least 2 grams per day to about 10 grams per day per about 10 to 25 milliliters of the mixture comprising the additional portion of the pre-treated biomass slurry, the hydrolyzed polysaccharide, the glycoside hydrolase, and water.

In some embodiments of step (iv), introducing an additional portion of the pre-treated biomass slurry to a mixture comprising the hydrolyzed polysaccharide and water under conditions sufficient to hydrolyze the polysaccharide present in the mixture can involve the introduction of the portion of biomass slurry at a rate from at least 2 grams per day to at least 20 grams per day, or 3 grams per day to about 20 grams per day, or from at least 4 grams per day to about 15 grams per day, or from about 5 grams per day to about 12 grams per day per about 30 milliliters of the mixture comprising the additional portion of the pre-treated biomass slurry, the hydrolyzed polysaccharide, the glycoside hydrolase, and water.

In some embodiments of step (iv), combining an additional portion of the pre-treated biomass slurry with a mixture comprising the hydrolyzed polysaccharide and water under conditions sufficient to hydrolyze the polysaccharide present in the mixture can be repeated for at least 2 days to at least 20 days. In some cases, step (iv), wherein the additional portion of the pre-treated biomass slurry is combined with a mixture comprising the hydrolyzed polysaccharide and water, can be repeated for at least 2 days to at least 18 days, or at least 3 days to at least 16 days, or at least 4 days to at least 14 days, or at least 5 days to at least 12 days, or at least 6 days to at least 10 days, or at least 7 days to at least 8 days. In certain embodiments, step (iv), wherein the additional portion of the pre-treated biomass slurry is combined with a mixture comprising the hydrolyzed polysaccharide and water, can be repeated for at least 4 days, or at least 4 days to at least 15 days, or at least 5 days to at least 10 days, or at least 6 days to at least 8 days.

In some embodiments of step (iv), the mixture comprising the additional portion of the pre-treated biomass slurry, the hydrolyzed polysaccharide, the glycoside hydrolase, and water is maintained under conditions sufficient to hydrolyze the polysaccharide present in the mixture for at least 1 day to at least 12 days. In some cases, step (iv), wherein the mixture comprising the additional portion of the pre-treated biomass slurry, the hydrolyzed polysaccharide, the glycoside hydrolase, and water, is maintained under conditions sufficient to hydrolyze the polysaccharide present in the mixture for at least 1 day to at least 10 days, or at least 2 days to at least 9 days, or at least 3 days to at least 8 days, or at least 4 days to at least 7 days, or at least 5 days to at least 6 days. In certain embodiments, step (iv), wherein the mixture comprising the additional portion of the pre-treated biomass slurry, the hydrolyzed polysaccharide, the glycoside hydrolase, and water, is maintained under conditions sufficient to hydrolyze the polysaccharide present in the mixture for at least 1 day, or at least 2 days, or at least 2 to at least 7 days, or at least 2 days to at least 5 days, or at least 2 days to at least 4 days.

The method of adding to the mixture comprising the hydrolyzed polysaccharide and an additional portion of the pre-treated biomass slurry of step (i), and maintaining the mixture comprising the hydrolyzed polysaccharide and the sugar composition under conditions sufficient to hydrolyze the polysaccharide present in the mixture can involve the introduction of the additional portion of the pre-treated biomass slurry at a rate from at least 1 gram per day to about 60 grams per day per about 10 to 300 milliliters of the mixture comprising the additional portion of the pre-treated biomass slurry, the hydrolyzed polysaccharide, the glycoside hydrolase, and the sugar composition.

In some embodiments of step (iv), introducing an additional portion of the pre-treated biomass slurry to the hydrolyzed polysaccharide and the sugar composition under conditions sufficient to hydrolyze the polysaccharide present in the mixture can involve the introduction of the additional portion of the pre-treated biomass slurry at a rate from at least 2 grams per day to about 50 grams per day per about 15 to 250 milliliters of the mixture comprising the additional portion of the pre-treated biomass slurry, the hydrolyzed polysaccharide, the glycoside hydrolase, and the sugar composition, or from at least 2 grams per day to about 45 grams per day per about 20 to 200 milliliters of the mixture comprising the additional portion of the pre-treated biomass slurry, the hydrolyzed polysaccharide, the glycoside hydrolase, and the sugar composition, or from at least 2 grams per day to about 40 grams per day per about 30 to 100 milliliters of the mixture comprising the additional portion of the pre-treated biomass slurry, the hydrolyzed polysaccharide, the glycoside hydrolase, and the sugar composition, or from at least 2 grams per day to about 35 grams per day per about 20 to 60 milliliters of the mixture comprising the additional portion of the pre-treated biomass slurry, the hydrolyzed polysaccharide, the glycoside hydrolase, and the sugar composition, or from at least 2 grams per day to about 30 grams per day per about 10 to 40 milliliters of the mixture comprising the additional portion of the pre-treated biomass slurry, the hydrolyzed polysaccharide, the glycoside hydrolase, and the sugar composition.

In some embodiments of step (iv), introducing an additional portion of the pre-treated biomass slurry to the hydrolyzed polysaccharide and the sugar composition under conditions sufficient to hydrolyze the polysaccharide present in the mixture can involve the introduction of the additional portion of the pre-treated biomass slurry at a rate from at least 2 grams per day to at least 40 grams per day, or 4 grams per day to about 30 grams per day, or from at least 5 grams per day to about 20 grams per day, or from about 6 grams per day to about 15 grams per day per about 60 milliliters of the mixture comprising the additional portion of the pre-treated biomass slurry, the hydrolyzed polysaccharide, the glycoside hydrolase, and the sugar composition.

In some embodiments of step (iv), combining an additional portion of the pre-treated biomass slurry with a mixture comprising the hydrolyzed polysaccharide and the sugar composition under conditions sufficient to hydrolyze the polysaccharide present in the mixture can be repeated for at least 1 day to at least 12 days. In some cases, step (iv), wherein the additional portion of the pre-treated biomass slurry is combined with a mixture comprising the hydrolyzed polysaccharide and water, can be repeated for at least 1 day to at least 10 days, or at least 2 days to at least 9 days, or at least 3 days to at least 8 days, or at least 4 days to at least 7 days, or at least 5 days to at least 6 days. In certain embodiments, step (iv), wherein the additional portion of the pre-treated biomass slurry is combined with a mixture comprising the hydrolyzed polysaccharide and water, can be repeated for at least 1 day, or at least 2 days, or at least 2 to at least 10 days, or at least 3 days to at least 8 days, or at least 5 days to at least 7 days.

In some embodiments of step (iv), the mixture comprising the additional portion of the pre-treated biomass slurry, the hydrolyzed polysaccharide, the glycoside hydrolase, and the sugar composition is maintained under conditions sufficient to hydrolyze the polysaccharide present in the mixture for at least 1 day to at least 12 days. In some cases, step (iv), wherein the mixture comprising the additional portion of the pre-treated biomass slurry, the hydrolyzed polysaccharide, the glycoside hydrolase, and the sugar composition, is maintained under conditions sufficient to hydrolyze the polysaccharide present in the mixture for at least 1 day to at least 10 days, or at least 2 days to at least 9 days, or at least 3 days to at least 8 days, or at least 4 days to at least 7 days, or at least 5 days to at least 6 days. In certain embodiments, step (iv), wherein the mixture comprising the additional portion of the pre-treated biomass slurry, the hydrolyzed polysaccharide, the glycoside hydrolase, and the sugar composition, is maintained under conditions sufficient to hydrolyze the polysaccharide present in the mixture for at least 1 day, or at least 2 days, or at least 2 to at least 7 days, or at least 2 days to at least 5 days, or at least 2 days to at least 4 days.

The methods of producing a polysaccharide hydrolysate from biomass can be performed in a continuous processing mode, wherein the hydrolysate can be used for downstream processing (i.e., fermentation). In other embodiments, the methods for producing a polysaccharide from biomass can involve using a small portion of hydrolysate for continuous saccharification. In some embodiments of the invention, the method of introducing a portion of biomass slurry and/or an additional portion of biomass slurry is performed continuously.

Fermentation

The sugar compositions produced in a hydrolysis step (saccharification) can be fermented. Accordingly, some embodiments of the invention provide a method for converting a sugar composition to a fermentation product, wherein the method includes fermenting a mixture containing a sugar composition and an ionic liquid or mixture of ionic liquids under conditions suitable to produce the fermentation product according to the methods described herein.

In some embodiments, a pre-fermentation saccharification is performed, and then a simultaneous saccharification and fermentation (SSF) is performed. Pre-fermentation saccharification can be conducted, for example, at a temperature ranging from about 20° C. to about 70° C., or from about 30° C. to about 65° C., or from about 35° C. to about 60° C., or from about 40° C. to about 57° C., or from about 35° C. to about 57° C., or from about 30° C. to about 55° C., or from about 40° C. to about 50° C., or from about 45° C. to about 50° C. Enzymatic hydrolysis of the pre-fermentation saccharification can be conducted at about 40° C., about 45° C., or about 50° C., or about 55° C. for at least about 10, 20, 30, 60, or 90 minutes or for at least about 2, 3, 4, 5, 6, 7, 8, 9, 10, 11, 12, 24, 48, or 72 hours. Accordingly, the SSF can be performed, for example, following the pre-fermentation saccharification step in which the sugar composition mixture produced from the pre-fermentation saccharification step is maintained at conditions sufficient to perform the fermentation step. In some embodiments, the temperature suitable for saccharification is decreased to at least 20° C., or 25° C., or 30° C., or 35° C., or 40° C. In certain embodiments, the temperature for fermentation in the SSF method is 30° C., or 37° C., or 40° C.

In certain embodiments, fermenting the sugar composition is conducted without removing the ionic liquid from the pre-treatment mixture and/or the sugar composition mixture. In some cases, fermenting the sugar composition is conducted without removing more than about 50%, or 40%, or 30%, or 20% or 10%, or 5%, or 1% of the ionic liquid from the pre-treatment mixture and/or the sugar composition mixture. In certain embodiments, the fermentation mixture contains at about 50% to about 99% of the ionic liquid present in the pre-treatment mixture, or the sugar composition mixture, or both. The fermentation mixture can contain about 50% to about 95%, or about 50% to about 90%, or about 55% to about 85%, or about 60% to about 80%, or about 65% to about 75% of the ionic liquid present in the pre-treatment mixture, or the sugar composition mixture, or both. In some embodiments, the fermentation step is conducted in the mixture containing the ionic liquid and the fermentable sugars resulting from step iv) of the method described above. In some embodiments, fermenting the sugar composition comprises adding a fermentation microorganism to the mixture containing the sugar composition and the ionic liquid or mixture of ionic liquids.

In some embodiments, *E. coli* or a yeast, such as *Saccharomyces cerevisiae* is used for fermenting the sugar composition in a fermentation conducted without removing the ionic liquid. In some embodiments, fermenting the sugar composition includes producing methanol, ethanol, isopropanol, butanol, isopentenol or a bisabolene. In some embodiments, the bisabolene is (E)-1-methyl-4-(6-methyl-hepta-2,5-dien-2-yl)cyclohex-1-ene; (S)-1-methyl-4-(6-methylhepta-1,5-dien-2-yl)cyclohex-1-ene; (Z)-1-methyl-4-(6-methylhept-5-en-2-ylidene)cyclohex-1-ene; or a mixture thereof. The methods of the invention can produce an amount of fermentation product equivalent to at least about 40% and less than 100% of theoretically available glucose monomers or xylose monomers, or a mixture thereof from the pre-treatment mixture comprising the biomass and the ionic liquid. In some embodiments of the invention, an amount of fermentation product equivalent to at least about 50% to about 99%, or 55% to about 95%, or about 55% to about 90%, or about 55% to about 85%, or about 60% to about 99%, or about 60% to about 95%, or about 60% to about 90%, or about 60% to about 85% of the theoretically available glucose monomers or xylose monomers, or the combination thereof from the pre-treatment mixture comprising the biomass and the ionic liquid is produced.

Example 1

Introduction

We report here a one-pot HG production of ethanol using bio-derived ILs (bionic liquids). For the first time, an ethanol titer of over 40 g L$^{-1}$ from lignocellulosic biomass at >30 wt % loading was achieved using an integrated fed-batch strategy with a one-pot process that combined pre-treatment, saccharification, and fermentation (PSF). The resulting reduction in water consumption and improved overall process economics serve as important steps toward more affordable and sustainable second-generation biofuels.[16,17]

Results and Discussion

Glucose Profiles from Bionic Liquids Treated Corn Stover

Figure 6:
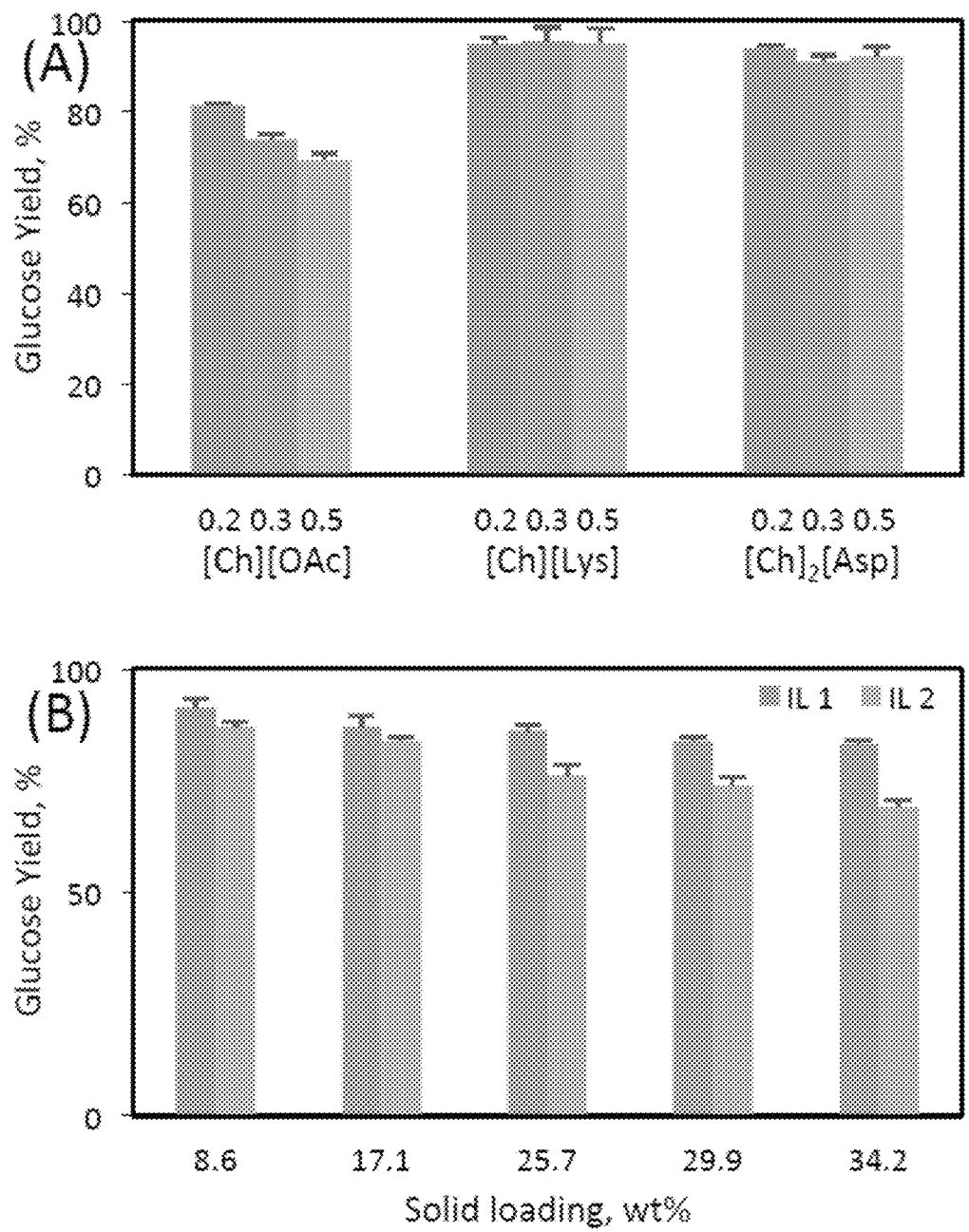
FIG. 6. Glucose yields from saccharification of choline-based ionic liquid 41: [Ch][Lys]; IL 2: [Ch]$_2$[Asp]) pre-treated corn stover. (A) Glucose yields with different ratios (R: 0.2, 0.3, and 0.5) of biomass to ionic liquid loading in pre-treatment; (B) Glucose yield after pre-treatment with solid loading from 8.6 to 34.2 wt %.

Three choline-based ILs, including cholinium acetate ([Ch][OAc]), cholinium lysinate ([Ch][Lys]), and cholinium aspartate ([Ch]$_2$[Asp]), were compared in terms of sugar titers as well as conversion yields. Recent reports on [Ch][OAc] and [Ch]$_2$[Asp] showed high levels of lignin extraction,[18,19] and another study of switchgrass pre-treatment with [Ch][Lys] and [Ch][OAc] showed that over 80% of glucose could be obtained after enzymatic hydrolysis.[15] Since pre-treatment with neat IL can suffer from poor mass/heat transfer at high solids loading, IL-water mixtures were used instead for biomass pre-treatment. FIG. 6 presents a summary of the sugar yields after a one-pot, two-step (pre-treatment and saccharification) process at different biomass loading levels. Compared to previous studies in which the ratios of biomass loading to ionic liquid loading ($R_{m/i}$) ranged from 0.05 to 0.1,[15,19] the results suggest that the dilute IL pre-treatment was also effective at a relatively higher $R_{m/i}$. For example, at 10% IL levels and a $R_{m/i}$ of 0.2, [Ch][OAc] yielded 81.4% glucose, whereas [Ch][Lys] and [Ch]$_2$[Asp] yielded over 90% glucose. The sugar yield from [Ch][OAc] pre-treatment decreased to below 70% when the $R_{m/i}$ increased to 0.5 (FIG. 6A). A successful one-pot PSF requires that the IL content in pre-treatment be as low as possible, therefore it is not possible to employ a low $R_{m/i}$ (e.g., less 1) in an HS process with solid loading over 20 wt %. The results obtained here indicated that [Ch][OAc] is not suitable for the proposed one-pot HG process. With the pre-treatment using [Ch][Lys] and [Ch]$_2$[Asp], glucose yield decreased as a function of increased solids loading (FIG. 6B). We attribute these results to poor mass transfer that significantly lowered pre-treatment efficiency. As shown in FIG. 6B, over 80% of glucose was recovered from the initial biomass after pre-treatment with [Ch][Lys] at solid loading of 34.2 wt % (equivalent to a glucan loading of 11.6 wt %). Using [Ch]$_2$[Asp], 73.9% of glucose was obtained with pre-treatment at a solid loading of 29.9 wt % (equivalent to a glucan loading of 10.2 wt %).

Figure 7:
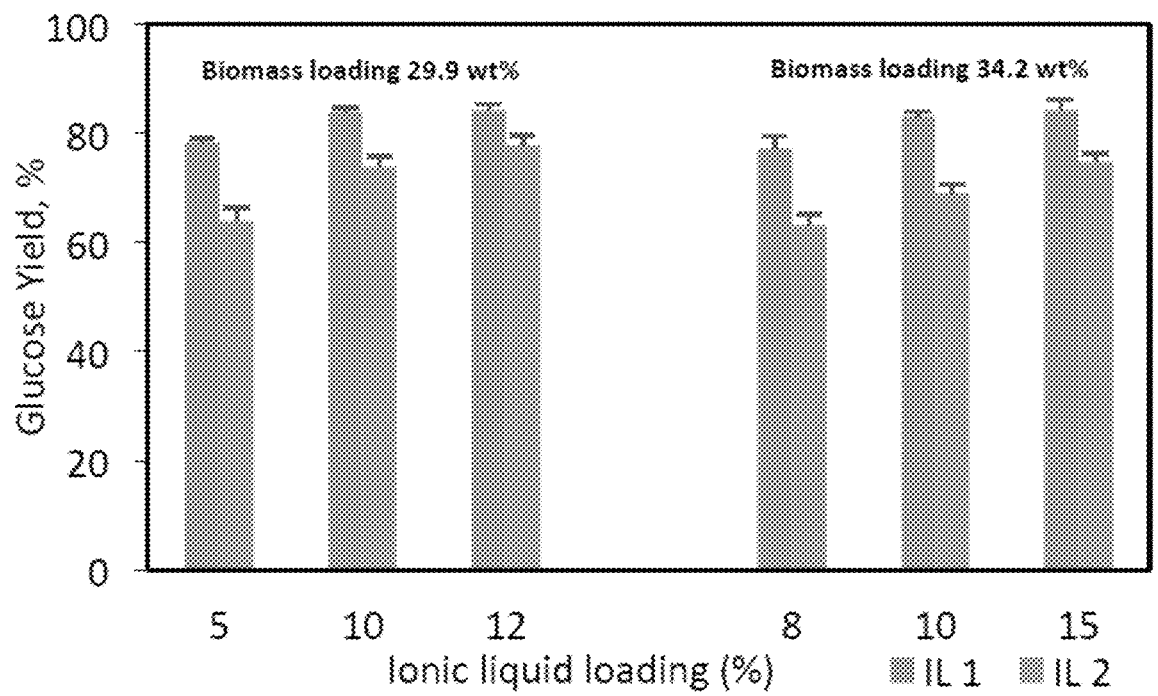
FIG. 7. Glucose yields from saccharification of choline-based ionic liquids (IL1: [Ch][Lys]; IL 2: [Ch]$_2$[Asp]) pre-treated corn stover (mass loading of 29.9 wt % and 34.2 wt %) with different ionic liquid loading.

Optimization of HS Bionic Liquid Pre-Treatment: Effect of IL Concentration and Biomass Loading on Glucan Saccharification Compared to traditional neat IL pre-treatment, in which IL is used for biomass dissolution (e.g., 1-ethyl-3-methyl-imidazolium acetate),[20] pre-treatment of biomass using an IL:water mixture does not go through the process of cellulose dissolution and regeneration. We hypothesize that the lignin extraction that occurs during pre-treatment using these IL:water mixtures that makes the crystalline cellulose more accessible to hydrolytic enzymes. The effect of IL concentration on HS pre-treatment and saccharification was investigated. FIG. 7 presents the glucose yields from both [Ch][Lys] and [Ch]$_2$[Asp] pre-treatment followed by the corresponding enzymatic hydrolysis. The increase of IL loading resulted in an increase in the capacity of lignin extraction, leading to improved pre-treatment efficiency as well as cellulose digestibility. The results indicate that an increase in [Ch][Lys] loading did contribute significantly to an increase in glucose yields, especially when the IL loading increased from 5 to 10 wt % (FIG. 7). As the IL loading further increased to 12 wt % or 15 wt %, the hydrolysis yield did not increase proportionally. With [Ch]$_2$[Asp] pre-treatment, the cellulose conversion efficiency increased with increases in IL loading. Further investigation of the IL concentration effect on fermentation was conducted and the results are discussed in the fermentation optimization section.

Response surface methodology was then employed to study how the IL loading and biomass loading together affect glucose yield after the two-step one-pot processing. FIG. 1 presents modelled 3-D plots of glucose yields from corn stover pre-treated with [Ch][Lys] (FIG. 1A) and [Ch]$_2$[Asp] (FIG. 1B), and the model analysis suggests that the interaction between IL loading and mass loading was significant. As shown in FIG. 1A, a [Ch][Lys] loading over 10 wt % could yield a relatively high glucose yield (>80%) at a solid loading over 30 wt %. Further increases in IL loading did not significantly increase glucose yield at the high solid-loading level (e.g., more than 30 wt %), indicative of poor mass/heat transfer during the HS processing. It was also noticed that the corn stover was only wetted without mobile liquids (water not sequestered in the plant cell wall) when the solid loading was increased to over 40 wt % due to the hygroscopic characteristics of corn stover that limit the availability of mobile water by sequestration of water in the cell wall.[21] For [Ch] [Asp] pre-treatment, further increases in IL loading (15 wt %) increased the glucose yield to around 80% at 30 wt % of solid loading (FIG. 1). This condition was then used for downstream processing.

Figure 2:
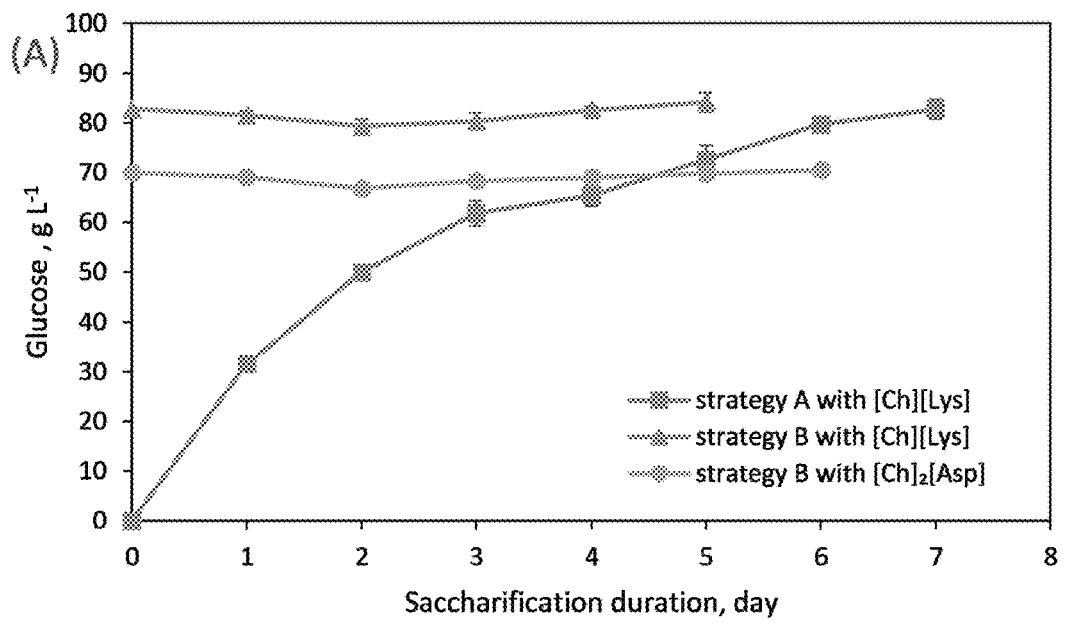
FIG. 2. Fed-batch high-solid saccharification of ionic liquid pre-treated corn stover. (A) Glucose profiles with two fed-batch strategies (■: Feeding [Ch][Lys] pre-treated corn stover with strategy A; ▲: Feeding [Ch][Lys] pre-treated corn stover with strategy B; ●: Feeding [Ch]$_2$[Asp] pre-treated corn stover with strategy B. The concentration was sampled and measured right before each feeding.); (B) Illustration of fed-batch strategy A&B.
Figure 2:
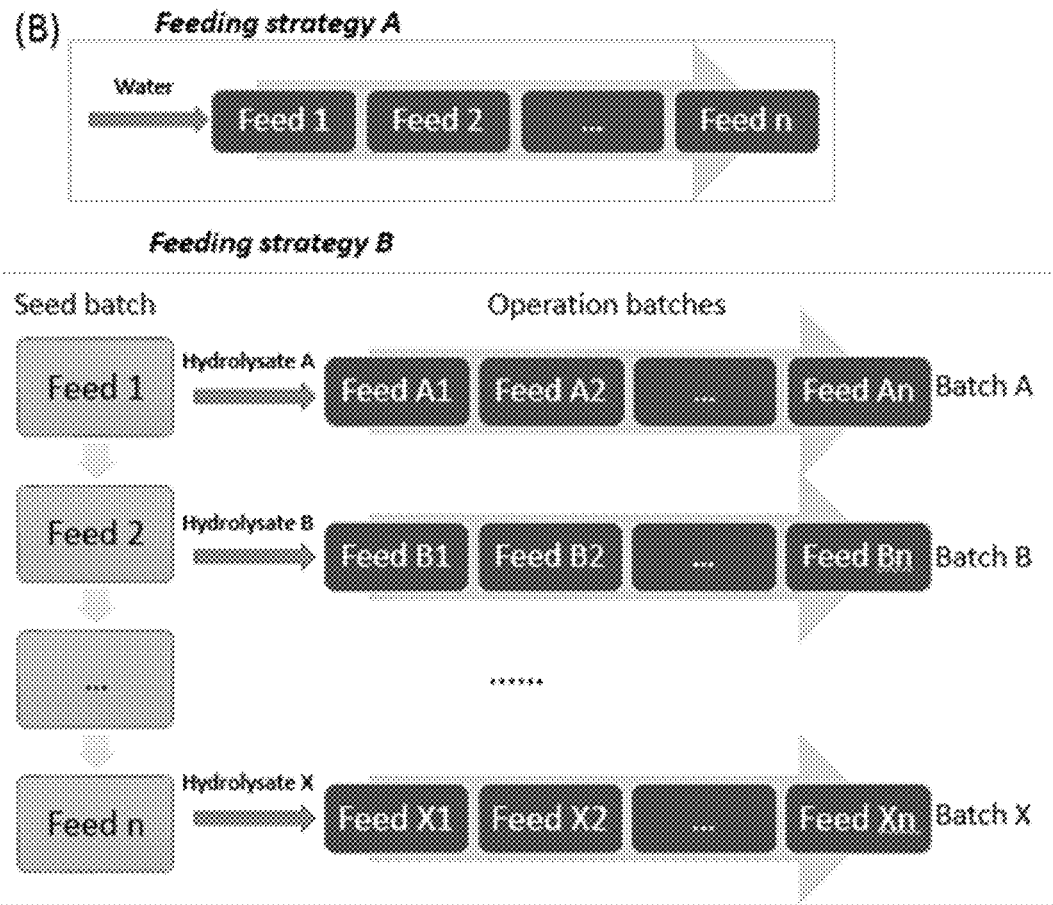

One Process Development for Concentrated Hydrolysates with Fed-Batch Saccharification In order to realize a robust one-pot conversion platform, a fed-batch approach is needed to achieve the desired fermentable sugar concentrations in the hydrolysates. Previous studies using high-solid water-washed steam-exploded corn stover reported 72.5% glucose yield with a sugar titer over 100 g $L^{-1}$.[11] In a one-pot system, however, the sugar titer and yield were limited by the solid loading used for pre-treatment. In order to reach the desired sugar titer (e.g., >80 g $L^{-1}$ glucose) using one-pot processing, a fed-batch strategy was employed and optimized after pre-treatment at 34.2 wt % solids loading at 140° C. for 3 hrs. As shown in FIG. 2, it took 6 days with 5 feeds (one initial feed plus one feed per day for the first 4 days) to reach a glucose titer of 80 g $L^{-1}$ with strategy A. In this process, the use of water at the beginning of saccharification is important for reducing viscosity as a requirement of efficient enzymatic hydrolysis of glucan and xylan. In a continuous processing mode, the hydrolysate could be primarily used for downstream processing such as fermentation and a small portion of the hydrolysate could be used for continuous saccharification by loading more pre-treated biomass. In batch mode, as is the case in this study, the use of water diluted the one-pot system and takes significantly longer time intervals to reach a concentrated hydrolysate, which is not favorable.

An improved strategy (strategy B) was to use the glucose hydrolysate from one batch of saccharification ("seed batch", as shown in FIG. 2B), in which the glucose titer was over 80 g $L^{-1}$, as a replacement for the water used in saccharification for all the other batches ("operation batches", as in FIG. 2B). As shown in FIG. 2A, with the initial loading of glucose hydrolysate, the glucose titer in each batch (e.g., Batch A in FIG. 2B) was maintained at a relatively high level and it took less time (e.g., 3 days in the fed-batch mode) to reach a desired sugar titer for fermentation comparing to the time used in strategy A (FIG. 2A). The improved feeding strategy was also applied for [Ch]$_2$ [Asp] pre-treated corn stover, where the hydrolysate in the seed batch contained 70 g $L^{-1}$ of glucose. As shown in FIG. 2A, the sugar titer was kept around 70 g $L^{-1}$ with one feeding per day for 6 days including additional 72 hours' saccharification for a complete digestion of glucan. Further optimization of the fed-batch saccharification was also conducted to improve the glucose productivity by adjusting the feeding strategy. For example, the feed rate of pre-treated biomass (in grams per day) was adjusted according to the digestion rate of cellulose during enzymatic hydrolysis. The results suggest that the sugar titer could be maintained after increasing the feed rate by 50%, which results in a 50% increase in terms of glucose productivity.

It was previously reported that an air-drying process could lower the moisture content in the pre-treated slurry, with a corresponding increased in glucose titer,[11] but it is unknown whether or not the drying process might change biomass structure (e.g., porosity) and further affect cellulose digestibility and/or if the resulting concentrated IL would affect fermentation efficiency. The energy consumption associated with air-drying is also an issue that prevented its use in this study. It is also worth mentioning that end-product inhibition (e.g., concentrated glucose and cellobiose) could affect the enzyme activity and further lower glucose yield.[12] Simultaneous saccharification and fermentation was thus incorporated into the one-pot system to improve the overall yield of glucose as well as ethanol.

Towards Sustainable Bioethanol Production Using One HG Process

Simultaneous saccharification and fermentation is a frequent practice for cellulosic ethanol production, which is favored to reduce end-product inhibition of enzymatic hydrolysis and increase productivity.[12] Previous studies using SSF reported successful ethanol production from cellulosic biomass.[22] Since the optimized temperature for enzymatic hydrolysis (e.g., 50° C.) and yeast-ethanol fermentation (e.g., 30° C. when using wild type yeast) are different, developing a controlled temperature strategy is critical for a successful high-solid fed-batch SSF. For example, a recent study using delayed SSF, in which the initial temperature was 45° C. for 12 hours pre-saccharification and was then cooled to 30° C. for SSF, showed improved yield and productivity.[23] Constant temperature (~37° C.) has also been used for high solid fed-batch SSF from sugarcane bagasse.[24] In order to increase fermentation productivity, it is imperative that the substrate viscosity be reduced at the early stage of SSF. Pre-saccharification at 50° C. for 24 hours was employed after feeding all the HS content biomass slurry. The effect of temperature on the performance of fed-batch SSF (FB-SSF) was then investigated at a yeast inoculation of 0.2%. Two different temperatures, 30° C. and 37° C., were compared after the pre-saccharification stage. The results show that the FB-SSF at 37° C. yields 71.6% of ethanol, which is higher than at 30° C. (67.1%) in 72 h. A compositional analysis of the residue after fermentation showed that 13.7% of cellulose was remained at 30° C., whereas only 10.2% of cellulose was remained at 37° C. This difference in undigested cellulose indicates that the low conversion yield is due to the fact that the saccharification rate was lower at a relatively low temperature (30° C.).

Figure 3:
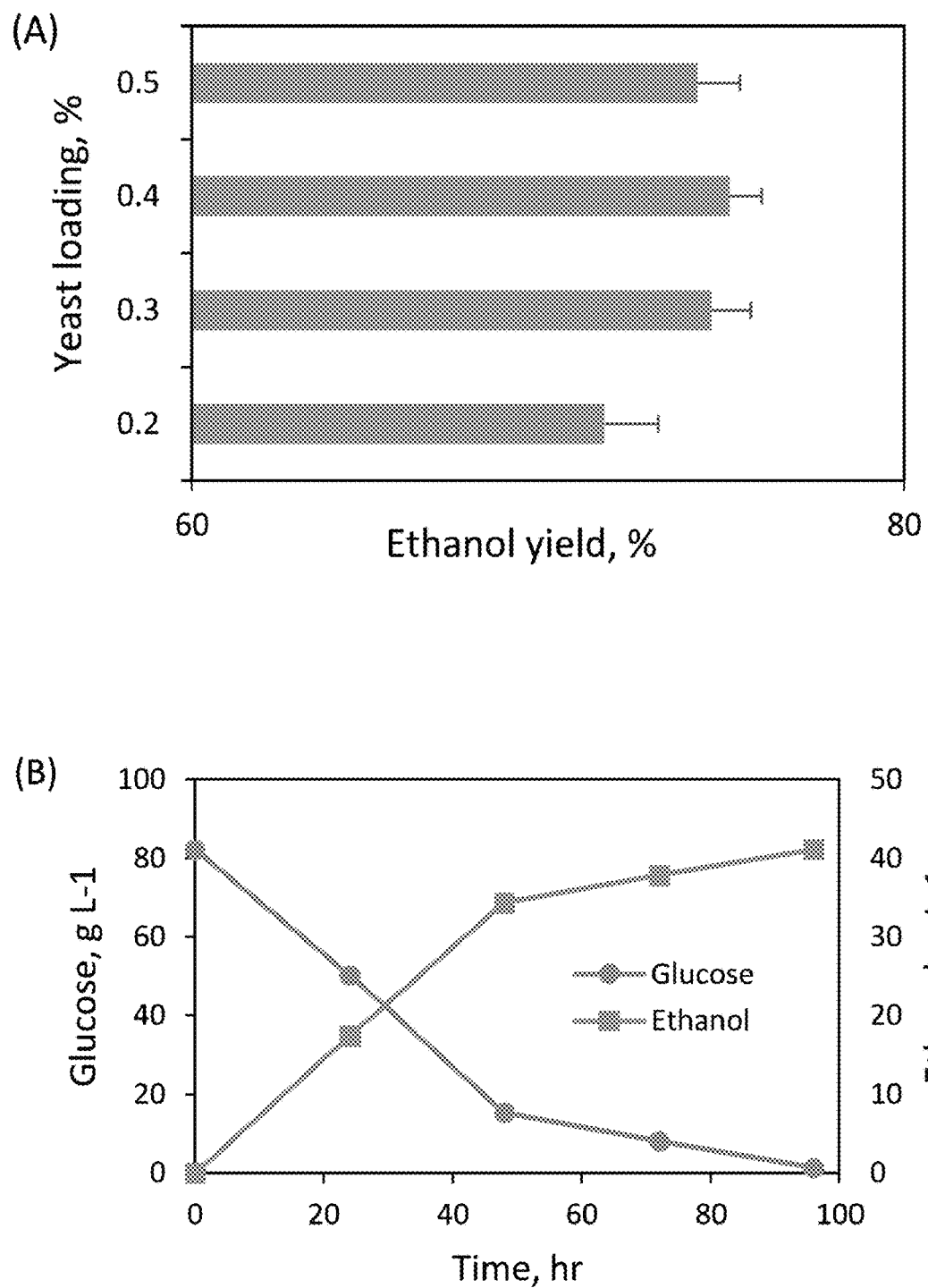
FIG. 3. Process optimization of one-pot high-gravity ethanol fermentation after [Ch] [Lys] pre-treatment. (A) Effect of yeast loading on ethanol fermentation; (B) Illustration of the glucose consumption and ethanol production during simultaneous saccharification and fermentation in the one-pot system.

Yeast loading was also investigated, as shown in FIG. 3A. Previous study of SSF using relatively low solid-loading biomass (~10%) suggested an optimal yeast loading of 1-2 g $L^{-1}$ yeast cell[25]. In the current study, the ethanol yield was lower when using 1 g $L^{-1}$ than that using higher yeast loading, and that ethanol fermentation was incomplete (at 72 hr) when the yeast loading was below 1 g $L^{-1}$ (data not shown). This indicates that the low yeast loading resulted in stuck fermentation. FIG. 3A also suggests that there is no significant difference in ethanol yield when the yeast loading increased from 3 to 5 g $L^{-1}$. In addition, when the biomass feeding amount was doubled in FB-SSF, the ethanol yield and titer were 41.1 g $L^{-1}$ and 74.8%, respectively (FIG. 3B), indicating that the one-pot process is stable at higher biomass loading levels and that the process of continuous feeding is possible. In the case of the batch process, the ethanol productivity was 0.7 g $L^{-1}$ $h^{-1}$ during the first 48 h and then decreased because of the depletion of glucose after 48 h.

Figure 4:
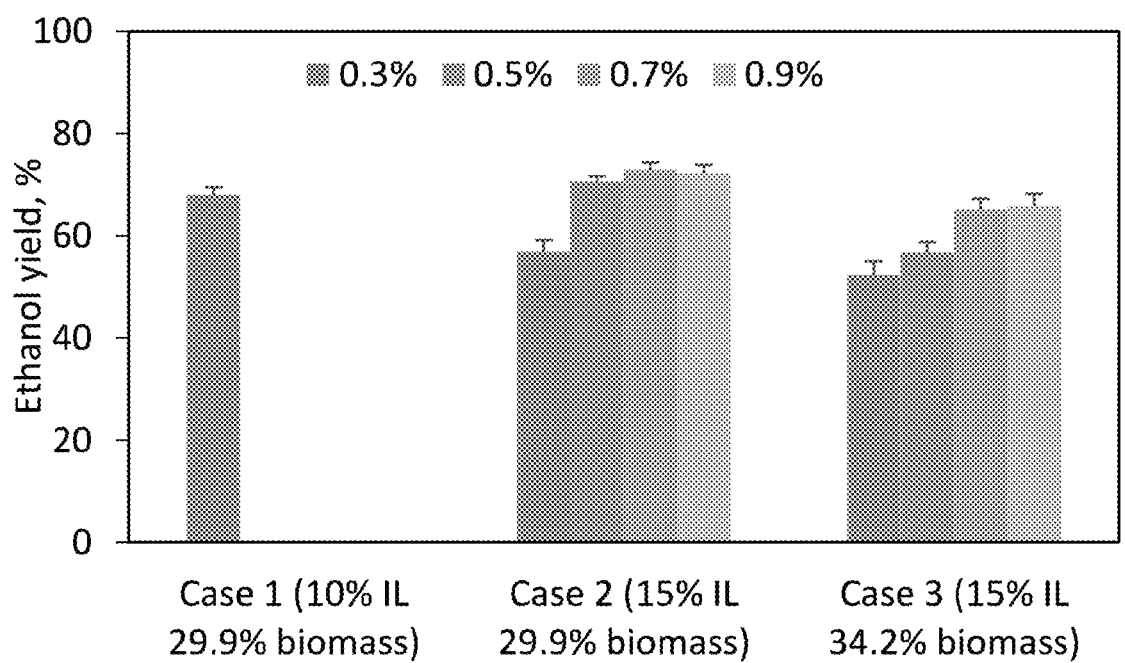
FIG. 4. Ethanol yield of [Ch]$_2$[Asp] pre-treated corn stover with increasing yeast inoculation (0.3%, 0.5%, 0.7%, and 0.9%). Case 1: as reference, using 10% (in weight, same as below) of ionic liquid and 29.9% of biomass loading; Case 2: using 15% of ionic liquid and 29.9% of biomass loading; Case 3: using 15% of ionic liquid and 34.2% of biomass loading.

As discussed previously, increasing the [Ch]$_2$[Asp] concentration to over 10 wt % during pre-treatment led to an increased glucose yield. As shown in FIG. 4, the [Ch]$_2$[Asp] concentration played an important role for the one-pot ethanol fermentation. The increase of [Ch]$_2$[Asp] concentration in pre-treatment significantly decreased the ethanol yield to about 50%, and the residual glucose suggested that the fermentation was incomplete at 96 h because of the low productivity. The decrease in ethanol yield could be due to the increased osmolarity that might lead to cell shrinkage and decreased cell viability.[2] Increases in yeast loading increased ethanol yield at the elevated $[Ch]_2[Asp]$ loading (15 wt %) (FIG. 4). At the same solids loading (29.9 wt %), increasing the yeast loading to 0.7% yielded 72.2% of ethanol (34.2 g $L^{-1}$). However, further increases in solids loading generated lower ethanol yields.

Figure 5:
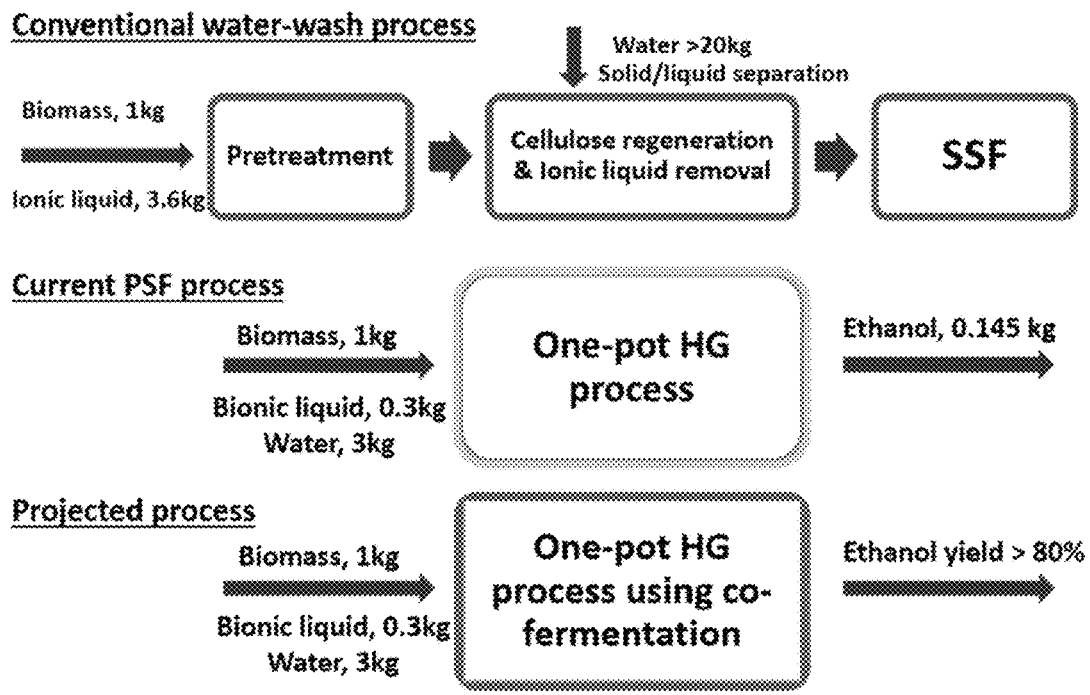
FIG. 5. Comparison of three scenarios in terms of water loading, ionic liquid (IL) loading, annual operating costs (AOC), and minimum ethanol selling price (MESP). Scenario 1. Conventional ionic liquid process, including a water-washing step before simultaneous saccharification and fermentation (SSF); Scenario 2. Current one-pot high-gravity (HG) PSF (pre-treatment, saccharification, and fermentation) configuration for ethanol production from glucose; Scenario 3. Projected system based on the current one-pot high-gravity configuration plus co-fermentation of ethanol from both glucose and xylose.
Figure 5:
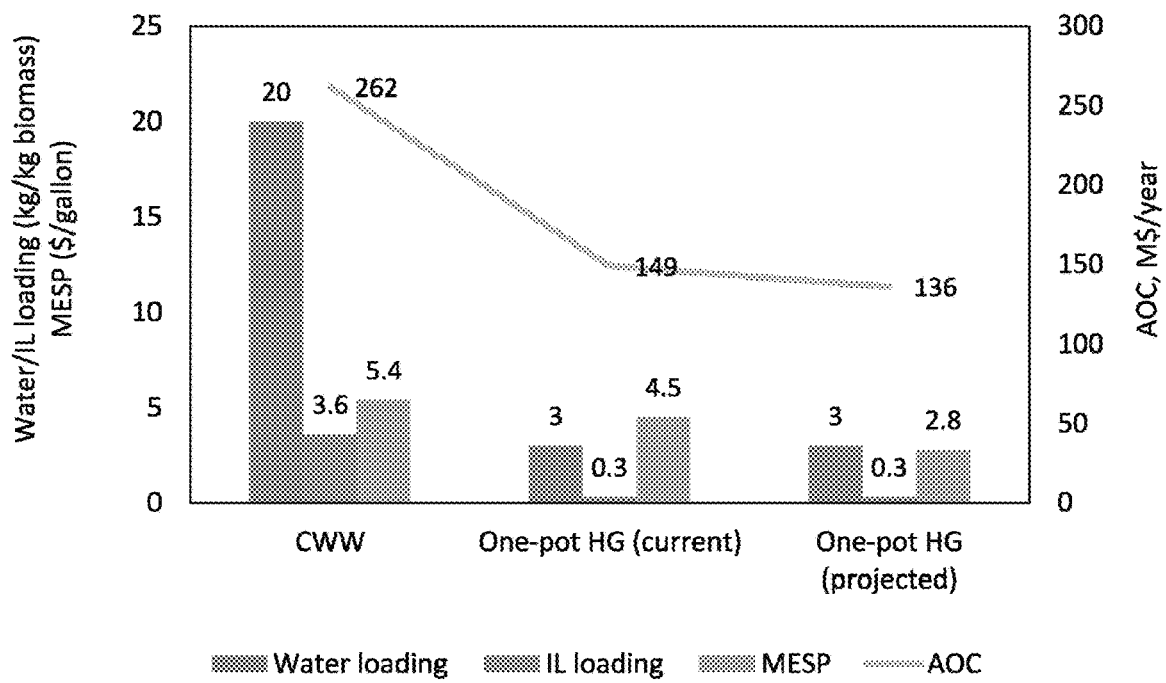

FIG. 5 shows a comparison of different scenarios. By eliminating the washing and solid/liquid separation steps, the one-pot process results in minimized water usage as low as 3 kg/kg of biomass. Our glucan/glucose balance suggests that over 90% of glucose from saccharification has been converted to ethanol, yielding an overall conversion of 74.8% in one-pot. As a result, 144.8 g ethanol was produced from the glucan present in 1 kg of corn stover. The one-pot system of fed-batch SSF could be enhanced for continuous ethanol fermentation with minimal modification. Besides the yeast-ethanol fermentation, the concentrated sugar stream from the HS fed batch process also provides flexibility for the other types of microbial conversion, which make it possible to convert for a broad range of fuels or chemicals at a relatively high titer in one pot. Integrated biomass processing strategies could be developed depending on the compatibility of IL and microbes as well as the downstream recovery pathway. For example, in situ product recovery (e.g., gas stripping)[26] could be applied to the fed batch system for continuous production of butanol. In addition, the utilisation the xylose in the hydrolysates could generate a more cost efficient process. For example, a microorganism that is capable of converting both glucose and xylose could utilize this concentrated sugar stream for improved biofuel yield.[27]

Production Cost Analysis

One-pot HG processing can significantly reduce the ethanol production cost compared to the conventional IL pre-treatment (e.g., 1-ethyl-3-methylimidazolium acetate) of biomass, as shown in FIG. 5. Previous techno-economic analyses of cellulosic ethanol production with IL pre-treatment[28,29] have identified the IL/biomass ratio as a critical factor that affects the minimum ethanol selling price (MESP) and concluded that the ratio must be below 2 to achieve an MESP below $5 $gal^{-1}$. The use of dilute IL (e.g., 10 wt % of [Ch][Lys]) for biomass pre-treatment in the current one-pot configuration reduced the usage of IL by decreasing the ratio from approximately 3.6 to 0.3. Consequently, the cost incurred due to unrecovered IL was much lower in the current one-pot process. The use of cholinium-based IL may also reduce cost because it can be synthesized from renewable sources, namely choline-hydroxide and lysine, using very straightforward processing and minimal separations. Another important factor that typically limits the large-scale IL processing of cellulosic biomass is the quantity of water required during production. Similar to the other pre-treatment technologies, conventional IL pre-treatment requires a detoxification step to remove IL and other inhibitors that are harmful for downstream saccharification and fermentation. The conventional IL process also requires an anti-solvent (e.g., water) for cellulose regeneration. This introduces additional processing steps such as water washing, filtration, and wastewater treatment. The use of a one-pot PSF strategy eliminates these steps and thus reduces capital and operating costs.

Figure 10:
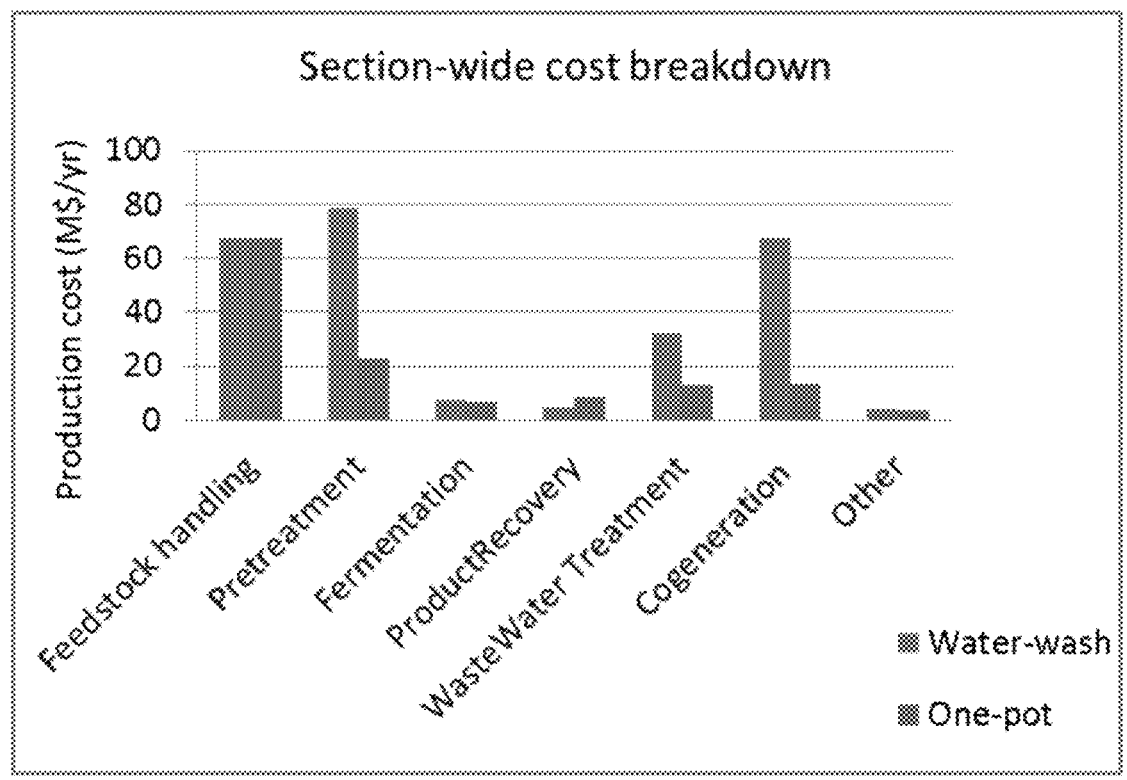
FIG. 10. Section wide production costs (including CapEx and OpEx).
Figure 11:
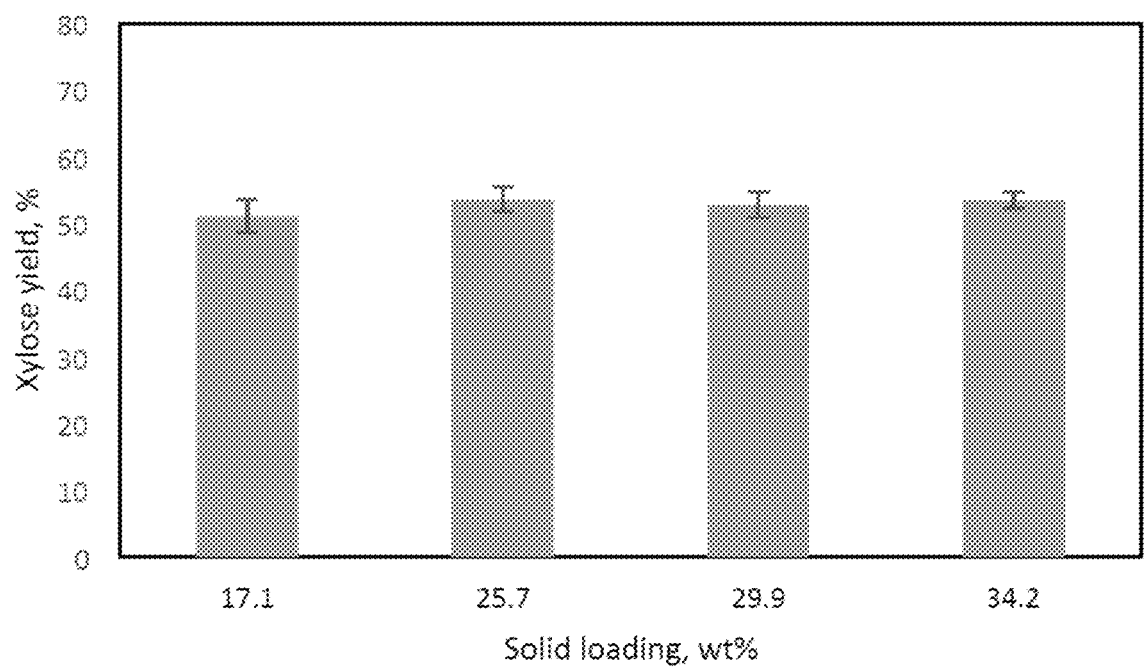
FIG. 11. Xylose yields from [Ch][Lys] pre-treated corn stover. The ionic liquid loading is 10%.
Figure 12:
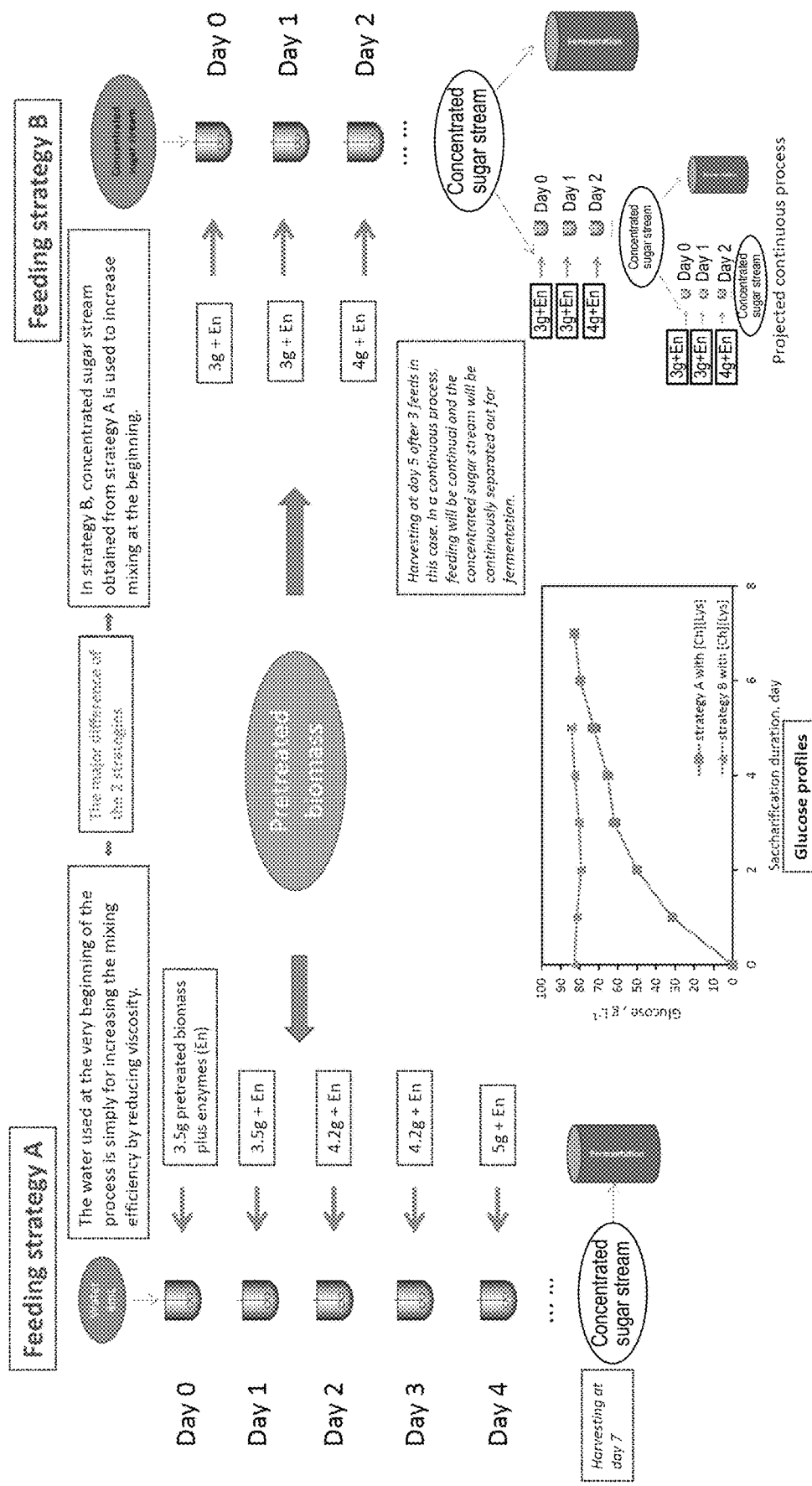
FIG. 12. Illustration of feeding strategy A and feeding strategy B.

As shown in FIG. 5, the water usage in the current HG configuration is reduced by greater than 85% relative to the conventional IL process, which reduces operating expenditures in the pre-treatment, wastewater treatment, and cogeneration sections (FIG. 10). The cost analysis as described in the methods section showed that the current one-pot HG process has the potential to reduce the annual operating cost (AOC) by more than 40% (FIG. 5). A cost analysis of co-fermentation using both glucose and xylose for ethanol production was also modelled and compared. The results of this projected co-fermentation case suggest that the MESP could be further reduced to approximately $2.8 $gal^{-1}$ (2014 USD).

CONCLUSIONS

For the first time, cellulosic ethanol was produced at a titer of over 40 g $L^{-1}$ in an optimized one-pot PSF process. The use of dilute bionic liquids enabled efficient pre-treatment of lignocellulosic biomass at a solid loading as high as 34.2 wt %, yielding over 80% glucose in one pot. The integrated one-pot PSF process combined with an improved feeding strategy effectively improved mass transfer without a dilution of the system and is able to continuously provide a concentrated glucose stream for ethanol production at high titer. The optimized ethanol yield and titer were 74.8% and 41.1 g $L^{-1}$, respectively. Benefiting from the high solid feeding strategy, the one-pot process significantly reduced water usage from up to 20 kg/kg corn stover in a conventional water-wash process to just 3 kg/kg (an 85% reduction) in a single vessel without intervention or clean-up. In a biorefinery utilising water recycling, the one-pot process provides substantial economic benefits through reduced IL inputs and wastewater generation. The resulting reductions in water demand, wastewater brine disposal, and energy-intensive chemical inputs have the potential to reduce GHG emissions and alleviate local environmental burdens. Compared to the conventional IL process, the economic analysis suggested that the current configuration could reduce the AOC by 40% (FIG. 5) with significant cost savings in terms of the MESP. These results establish a new approach to affordable, sustainable, and scalable biomass conversion using ionic liquids based on process intensification and integration.

EXPERIMENTAL

All of the chemicals were reagent grade and purchased from Sigma-Aldrich (St. Louis, MO) if not specified. The enzymes (Cellic® Ctec 2 and Htec 2) were given by Novozymes North America (Franklinton, NC), containing 188 mg protein per mL. Corn stover was supplied by the Department of Chemical Engineering & Materials Science at Michigan State University. The biomass was ground by a Thomas-Wiley Mini Mill fitted with a 20-mesh screen (Model 3383-L10 Arthur H. Thomas Co., Philadelphia, PA, USA) and analyzed for polysaccharide composition (glucan 34.1 wt % and xylan 25.1 wt %). Cholinium Acetate ([Ch][OAc]) was purchased from Sigma and used as received. Cholinium Lysinate ([Ch][Lys]) and Choline Aspartate ($[Ch]_2[Asp]$) were synthesized as reported[15,19].

Novel Dilute Bio-Derived Ionic Liquid Pre-Treatment

The pre-treatment was conducted in 50-mL pressure tube (Ace Glass Inc., Vineland, NJ, USA). In a typical HS pre-treatment (e.g., 30 wt %), for example, 3 g of corn stover was loaded in 10 g of IL/water solution with a certain IL concentration (e.g., 10 wt %). After a thorough mixing of IL, water, and biomass, the tube was submerged in an oil bath at 140° C. for 3 hours. The solid loading amount in this study is presented as a percentage ratio of dry biomass weight (g) to the weight of IL/water mixture (g). After pre-treatment, the slurry was cooled down to room temperature and the pH was adjusted to 5 by thoroughly mixing with hydrochloric acid before saccharification.

Enzymatic Saccharification

The saccharification was carried out at 50° C. and pH 5 at 48 rpm in a rotary incubator (Enviro-Genie, Scientific Industries, Inc.) using commercial enzyme mixtures, Cellic® CTec2 and HTec2, with an enzyme dosage of 20 mg protein per gram glucan and 2 mg protein per gram xylan, respectively. One-pot processing was employed and no IL separation was conducted. For the optimization of glucose yield, the one-pot process was conducted with additional water during saccharification for improving mixing and the solid content was around 10 wt %. In order to provide concentrated hydrolysates, fed-batch process was conducted depending on the solid loading used in pre-treatment. For example, with a basic feeding strategy (strategy A), 11.2 g pre-treated biomass slurry at solid loading of 34.2 wt % was separated into 3 loads (e.g., 3.5 g, 3.5 g, and 4.2 g) for loading every 24 hrs in 2 days into 4 mL initial solution (e.g., water). With an improved feeding strategy (strategy B), the initial water solution was replace with concentrated glucose solution (e.g., 80 g $L^{-1}$) from an independent batch ("seed batch", as shown in FIG. 2), and pre-treated biomass was continuously loaded into the seed batch for supplying hydrolysates to operation batches (e.g., batch A, B & C). Citric acid buffer (pH 5, 40 mM) was added to maintain the pH during the optimization.

Fermentation

*Saccharomyces cerevisiae* strain BY4741 (MATa his3Δ0 leu2Δ0 met15Δ0 ura3Δ0), a derivative of S288C was activated according to NREL procedure[30]. Yeast inoculation was initiated with the concentrated hydrolysates directly from saccharification. For an integrated one-pot ethanol SSF, the temperature was decreased after a 24 hours' pre-saccharification (50° C.), and the SSF was then conducted in an anaerobic condition at 120 rpm with specified temperature.

HPLC Analysis

In order to accurately determine the ethanol and sugar yield, the current study employed a reported method, in which the slurry sample was diluted extensively (at least 10 times)[31] and then measured by HPLC (Agilent HPLC 1200 Series) equipped with a Bio-Rad Aminex HPX-87H column and a Refractive Index detector. The solid fraction after saccharification or fermentation in a dilute solution is below 1 wt % after dilution and its volume displacement could then be negligible. The glucose yield is represented as a percentage of the initial glucose content in corn stover before processing; likewise, the ethanol yield is represented as a percentage of the theoretical amount from the initial glucose content in corn stover (e.g., theoretically, 0.511 gram ethanol per gram glucose).

Techno-Economic Analysis

Figure 8:
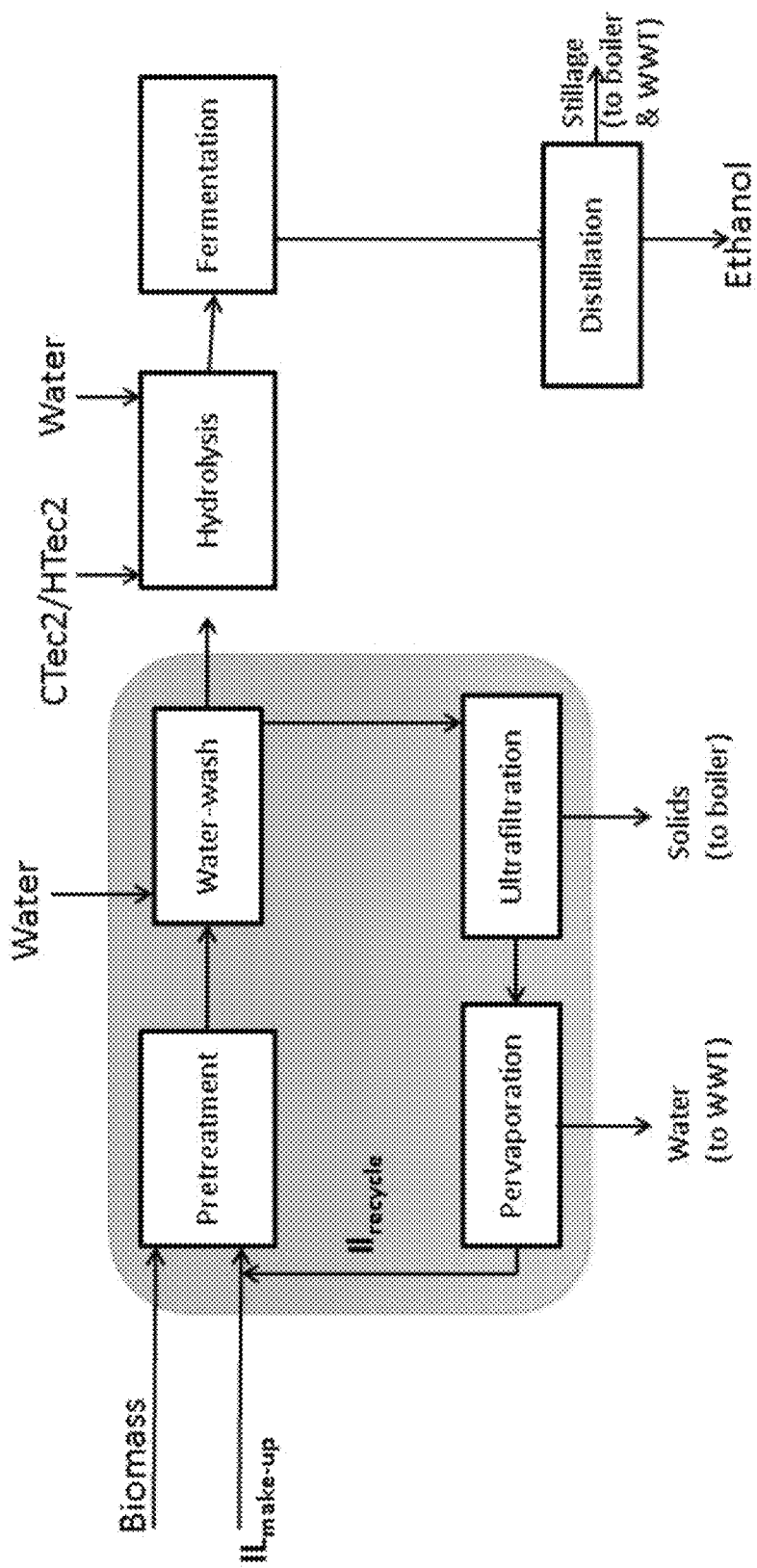
FIG. 8. Simplified block flow diagram of water-wash process configuration.
Figure 9:
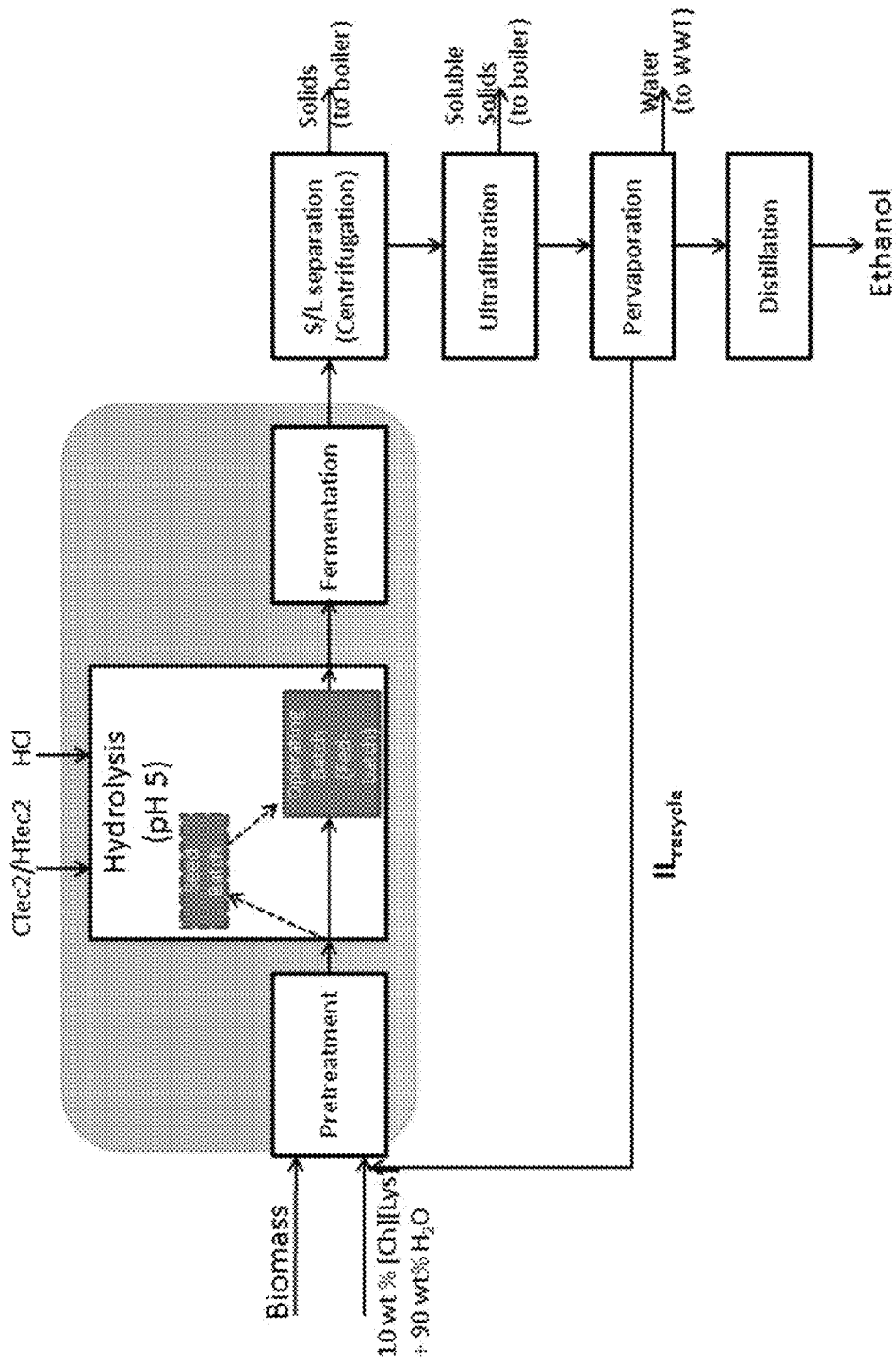
FIG. 9. Simplified block flow diagram of one pot HG process configuration.

To carry out the TEA, a detailed biorefinery model developed in SuperPro designer was used in this study (Table 1). The biorefinery model encompasses pre-treatment, hydrolysis, fermentation, product recovery, wastewater treatment, and an onsite co-generation facility. The plant was designed to process 2000 dry MT/day and most of the process and economic data were taken from a recent study by National Renewable Energy Laboratory (NREL)[10]. Consistent with the NREL study, the minimum ethanol selling price (MESP) was computed based on a detailed cash flow analysis with a 10% internal rate of return. The base year for economic analysis in the current study is 2014. In order to benchmark the economic performance of the one-pot HG process, a conventional IL process that involves a water-washing (WW) step prior to enzymatic hydrolysis was used as a reference scenario[29] (FIG. 8). Unlike the choline-based ILs used in the one-pot HG process, the WW process used 1-ethyl-3-methylimidazolium acetate, which is not compatible with commercial enzymes. Hence most of the IL (>99.9%) was removed from the pre-treated biomass using a water-intensive water-wash step. In an optimized WW process configuration with water recycling, water loading in the water-wash step (i.e., mass ratio between water used and biomass) could be as high as 20. The one-pot HG process using [Ch][Lys] was considered for comparison. For both of these processes, high IL recovery (>99.9%) was assumed, using pervaporation technology detailed in FIG. 8 and FIG. 9 (process flow diagrams for WW and one-pot configurations, respectively). To capture the economic merits of the one-pot process (FIG. 9), three process scenarios were constructed: one conventional scenario with co-fermenting microbes and two one-pot HG scenarios (without and with co-fermenting microbes, labelled as 'current' and 'projected' scenarios, respectively) (FIG. 5).

TABLE 1

Process and economic data for the three scenarios studied in the TEA.

| | Water-wash[a] | One-pot HG (current)[b] | One-pot HG (projected)[c] |
|---|---|---|---|
| Biomass processed (dry MT/day) | 2000 | 2000 | 2000 |
| Biomass price ($/dry ton, delivered at plant-gate) | 80 | 80 | 80 |
| Pre-treatment | | | |
| IL used | [C$_2$C$_1$Im][OAc] | [Ch][Lys] | [Ch][Lys] |
| IL purity (wt % of IL in aqueous IL solution [IL:H2O]) | 90 | 10 | 10 |
| IL/Biomass ratio (mass ratio on dry basis) | 3.6 | 0.29 | 0.29 |
| IL recovery (%) | 99.9 | 99.9 | 99.9 |
| IL price ($/kg) | 5 | 5 | 2 |
| Water loading (mass ratio between water and biomass in water-wash step in WW route) | 20 | N/A | N/A |

TABLE 1-continued

Process and economic data for the three scenarios studied in the TEA.

|  | Water-wash[a] | One-pot HG (current)[b] | One-pot HG (projected)[c] |
|---|---|---|---|
| Loss of glucan in water-wash step (wt % of initial glucan) | 5 | NONE | NONE |
| Loss of xylan in water-wash step (wt % of initial xylan) | 24 | NONE | NONE |
| Hydrolysis |  |  |  |
| Enzyme loading (mg/g glucan present in initial biomass) | 20 | 20 | 10 |
| Enzyme price ($/kg protein) | 4.29 | 4.29 | 4.29 |
| Glucan-to-glucose conversion (%) | 98 | 84 | 90 |
| Xylan-to-xylose conversion (%) | 79 | 80 | 90 |
| Fermentation |  |  |  |
| Co-fermentation of glucose and xylose | YES | NO (only Glucose) | YES |
| Glucose-to-ethanol conversion (%) | 95 | 90 | 90 |
| Xylose-to-ethanol conversion (%) | 60 | 0 | 90 |

[a]based on (Cruz et al. 2013, Li et al. 2013, Li et al. 2015, Shi et al. 2014, Uppugundla et al. 2014)
[b]constructed to represent the 'current' one-pot HG process in this study
[c]constructed to represent 'projected' one-pot HG process with perceived advances (esp. with yield and enzyme loading)

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

REFERENCES

1. B. Dien, M. Cotta and T. Jeffries, *Applied microbiology and biotechnology*, 2003, 63, 258-266.
2. R. Koppram, E. Tomás-Pejó, C. Xiros and L. Olsson, *Trends in biotechnology*, 2014, 32, 46-53.
3. M. Jin, C. Gunawan, N. Uppugundla, V. Balan and B. E. Dale, *Energy & Environmental Science*, 2012, 5, 7168-7175.
4. A. Mohagheghi, M. Tucker, K. Grohmann and C. Wyman, *Applied Biochemistry and Biotechnology*, 1992, 33, 67-81.
5. S. De, S. Dutta and B. Saha, *ChemSusChem*, 2012, 5, 1826-1833.
6. K. Nakashima, K. Yamaguchi, N. Taniguchi, S. Arai, R. Yamada, S. Katahira, N. Ishida, H. Takahashi, C. Ogino and A. Kondo, *Green Chemistry*, 2011, 13, 2948-2953.
7. E. Y. Park, K. Naruse and T. Kato, *Biotechnol Biofuels*, 2012, 5, 64.
8. M. Cantarella, L. Cantarella, A. Gallifuoco, A. Spera and F. Alfani, *Biotechnology progress*, 2004, 20, 200-206.
9. V. Balan, B. Bals, S. P. Chundawat, D. Marshall and B. E. Dale, in *Biofuels*, Springer, 2009, pp. 61-77.
10. D. Humbird, R. Davis, L. Tao, C. Kinchin, D. Hsu, A. Aden, P. Schoen, J. Lukas, B. Olthof and M. Worley, 2011.
11. Y. Lu, Y. Wang, G. Xu, J. Chu, Y. Zhuang and S. Zhang, *Applied biochemistry and biotechnology*, 2010, 160, 360-369.
12. Z. Xiao, X. Zhang, D. J. Gregg and J. N. Saddler, 2004.
13. J. Shi, J. M. Gladden, N. Sathitsuksanoh, P. Kambam, L. Sandoval, D. Mitra, S. Zhang, A. George, S. W. Singer and B. A. Simmons, *Green Chem.*, 2013, 15, 2579-2589.
14. X.-D. Hou, N. Li and M.-H. Zong, *Bioresource technology*, 2013, 136, 469-474.
15. N. Sun, R. Parthasarathi, A. M. Socha, J. Shi, S. Zhang, V. Stavila, K. L. Sale, B. A. Simmons and S. Singh, *Green Chemistry*, 2014, 16, 2546-2557.
16. R. Dominguez-Faus, S. E. Powers, J. G. Burken and P. J. Alvarez, *Environmental Science & Technology*, 2009, 43, 3005-3010.
17. M. Wu, M. Mintz, M. Wang and S. Arora, *Environmental management*, 2009, 44, 981-997.
18. F. Cheng, H. Wang, G. Chatel, G. Gurau and R. D. Rogers, *Bioresource technology*, 2014, 164, 394-401.
19. X. D. Hou, J. Xu, N. Li and M. H. Zong, *Biotechnology and bioengineering*, 2015, 112, 65-73.
20. C. Li, B. Knierim, C. Manisseri, R. Arora, H. V. Scheller, M. Auer, K. P. Vogel, B. A. Simmons and S. Singh, *Bioresource Technology*, 2010, 101, 4900-4906.
21. S. Viamajala, J. D. McMillan, D. J. Schell and R. T. Elander, *Bioresource Technology*, 2009, 100, 925-934.
22. F. Xu, K. Theerarattananoon, X. Wu, L. Pena, Y.-C. Shi, S. Staggenborg and D. Wang, *Industrial Crops and Products*, 2011, 34, 1212-1218.
23. L. Paulová, P. Patáková, M. Rychtera and K. Melzoch, *Fuel*, 2014, 122, 294-300.
24. X. Zhao, L. Dong, L. Chen and D. Liu, *Bioresource technology*, 2013, 135, 350-356.
25. K. Olofsson, M. Bertilsson and G. Lidén, *Biotechnol Biofuels*, 2008, 1, 1-14.
26. C. Xue, J. Zhao, F. Liu, C. Lu, S.-T. Yang and F.-W. Bai, *Bioresource Technology*, 2013, 135, 396-402.
27. S.-J. Ha, J. M. Galazka, S. R. Kim, J.-H. Choi, X. Yang, J.-H. Seo, N. L. Glass, J. H. Cate and Y.-S. Jin, *Proceedings of the National Academy of Sciences*, 2011, 108, 504-509.
28. D. Klein-Marcuschamer, C. Turner, M. Allen, P. Gray, R. G. Dietzgen, P. M. Gresshoff, B. Hankamer, K. Heimann, P. T. Scott and E. Stephens, *Biofuels, Bioproducts and Biorefining*, 2013, 7, 416-428.
29. N. M. Konda, J. Shi, S. Singh, H. W. Blanch, B. A. Simmons and D. Klein-Marcuschamer, *Biotechnology for biofuels*, 2014, 7, 86.

30. N. Dowe and J. McMillan, *National Renewable Energy Laboratory (NREL) Analytical Procedures,* 2008, NREL/TP-510-42630, Golden, CO, USA.
31. J. B. Kristensen, C. Felby and H. Jorgensen, *Applied biochemistry and biotechnology,* 2009, 156, 127-132.

What is claimed is:

1. A method of producing a polysaccharide hydrolysate from biomass, the method comprising:
   (i) providing a slurry comprising pre-treated biomass at a concentration of at least about 5% w/w and less than about 50% w/w, an ionic liquid or a mixture of ionic liquids at a concentration of between about 5% w/w and about 25% w/w, and water, wherein the ionic liquid or the mixture of ionic liquids and biomass are present in the pre-treated slurry at a mass ratio $R_{m/i}$ of from about 0.2 to about 5, and wherein the ionic liquid or the mixture of ionic liquids comprises:
      a) a choline cation; and
      b) an anion selected from the group consisting of a carboxylic acid anion, dicarboxylic acid anion, lysinate, hydroxide anion, bisulfate anion, dihydrogen phosphate anion, phosphate anion, bicarbonate anion, and chloride anion;
   (ii) combining a portion of the pre-treated biomass slurry with a glycoside hydrolase and a hydrolysate seed batch comprising a sugar and water, wherein the sugar is at a concentration of at least 70% w/w in the hydrolysate seed batch; and
   (iii) maintaining the mixture formed in step (ii) under conditions sufficient to hydrolyze the polysaccharide present in the portion of the pre-treated biomass slurry, thereby forming a mixture comprising a hydrolyzed polysaccharide;
   wherein the biomass comprises polysaccharide and lignin, and
   wherein at least 70% of glucan and/or xylan present in the biomass is converted into a monosaccharide.

2. The method of claim 1, wherein the portion of the pretreated biomass slurry of step (ii) is introduced at a rate of from at least 2 grams per day to about 20 grams per day per 30 milliliters of the mixture comprising the glycoside hydrolase and hydrolysate seed batch.

3. The method of claim 1, wherein the mixture of step (iii) is maintained under conditions sufficient to hydrolyze the polysaccharide for at least 1 day, or at least 2 days.

4. The method of claim 1, further comprising:
   (iv) adding to the mixture formed in step (iii) an additional portion of the pre-treated biomass slurry of step (i), and maintaining the mixture under conditions sufficient to hydrolyze the polysaccharide present in the additional portion of the pre-treated biomass slurry; and
   (v) repeating the step of (iv) 1 to 100 times.

5. The method of claim 4, wherein the additional portion of the pretreated biomass slurry of step (iv) is added at a rate of from at least 2 grams per day to about 20 grams per day per 30 milliliters of the mixture formed in step (iii).

6. The method of claim 5, wherein the addition of the portion of the pre-treated biomass slurry of step (iv) is repeated for at least 4 days.

7. The method of claim 4, wherein the mixture of step (iv) is maintained under conditions sufficient to hydrolyze the polysaccharide for at least 1 day, or at least 2 days.

* * * * *